(12) United States Patent
Grant et al.

(10) Patent No.: US 8,573,034 B2
(45) Date of Patent: *Nov. 5, 2013

(54) RESIDUE CONCENTRATION MEASUREMENT TECHNOLOGY

(75) Inventors: Donald C. Grant, Grand Marais, MN (US); Mark R. Litchy, Plymouth, MN (US)

(73) Assignee: CT Associates, Inc., Eden Prairie, MN (US)

( * ) Notice: Subject to any disclaimer, the term of this patent is extended or adjusted under 35 U.S.C. 154(b) by 253 days.

This patent is subject to a terminal disclaimer.

(21) Appl. No.: 13/068,396

(22) Filed: May 10, 2011

(65) Prior Publication Data

US 2011/0214489 A1 Sep. 8, 2011

Related U.S. Application Data

(63) Continuation-in-part of application No. 12/357,088, filed on Jan. 21, 2009, now Pat. No. 8,272,253.

(60) Provisional application No. 61/011,901, filed on Jan. 22, 2008.

(51) Int. Cl.
*G01N 1/28* (2006.01)

(52) U.S. Cl.
USPC ....... 73/61.72; 73/61.71; 73/61.63; 73/61.64; 73/61.62; 73/53.01; 73/1.02; 73/1.03

(58) Field of Classification Search
USPC .................................. 73/61.62–61.75, 1.03
See application file for complete search history.

(56) References Cited

U.S. PATENT DOCUMENTS

| 4,761,074 | A | * | 8/1988 | Kohsaka et al. ................ 356/37 |
| 4,794,086 | A | * | 12/1988 | Kasper et al. ................... 436/36 |
| 5,076,097 | A | * | 12/1991 | Zarrin et al. .................. 73/61.72 |
| 5,098,657 | A | * | 3/1992 | Blackford et al. .............. 422/73 |
| 5,247,842 | A | * | 9/1993 | Kaufman et al. ............. 73/865.5 |
| 6,491,872 | B1 | * | 12/2002 | Wick .............................. 422/72 |
| 6,620,620 | B1 | * | 9/2003 | Anderson et al. .............. 436/55 |
| 7,777,868 | B2 | * | 8/2010 | Blackford et al. .............. 356/37 |
| 8,272,253 | B2 | * | 9/2012 | Grant et al. ................... 73/61.72 |
| 2003/0110840 | A1 | * | 6/2003 | Arriaga et al. ............... 73/61.72 |
| 2008/0216563 | A1 | * | 9/2008 | Reed et al. .................... 73/61.71 |

OTHER PUBLICATIONS

Reply to Office Action dated Nov. 29, 2011, mailed Feb. 29, 2012 and filed in USPTO on Mar. 5, 2012, for U.S. Appl. No. 12/357,088, which includes ASTM Designation D 5127-07 "Standard Guide for Ultra-Pure Water Used in the Electronics and Semiconductor Industries".

* cited by examiner

*Primary Examiner* — Hezron E Williams
*Assistant Examiner* — Alexander Mercado
(74) *Attorney, Agent, or Firm* — Skinner & Associates

(57) ABSTRACT

A method and apparatus for measuring dissolved residue concentrations and particulate residue particle concentrations and size distribution in liquids, particularly colloidal suspensions. The method involves separating dissolved and particulate residues in liquids for subsequent analysis of the residue species. The method includes the steps of forming an aerosol from the liquid sample to be analyzed, evaporating the droplets in the aerosol to dryness, detecting and sizing the particles, and determining the liquid volumetric inspection rate. An apparatus for separating dissolved and particulate residues in liquids for determination of the concentrations of the two residue species as well as the size distribution of the particulate species is also disclosed. The apparatus includes a droplet former, a dryer communicatively connected to the droplet former, and a detector communicatively connected to the evaporator for detecting and sizing particles.

9 Claims, 22 Drawing Sheets

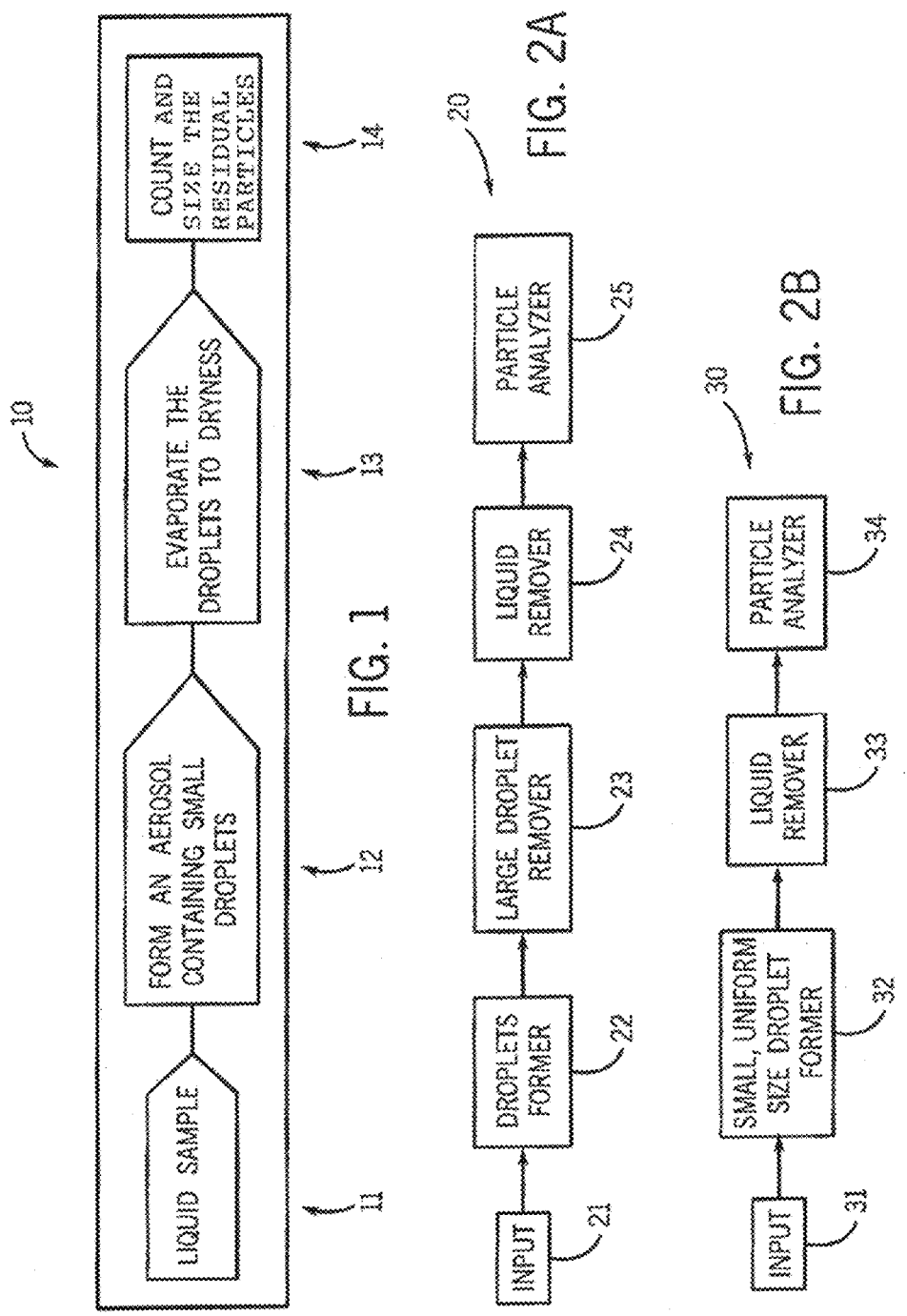

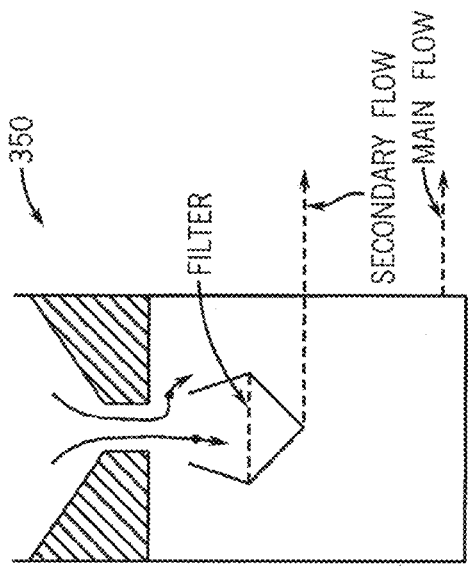
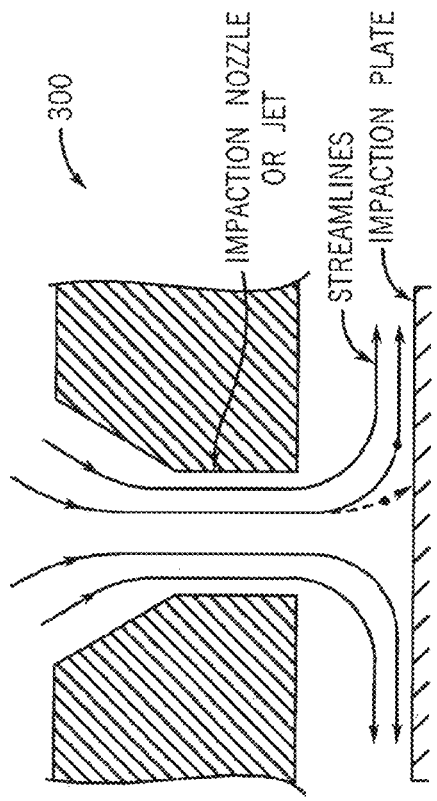
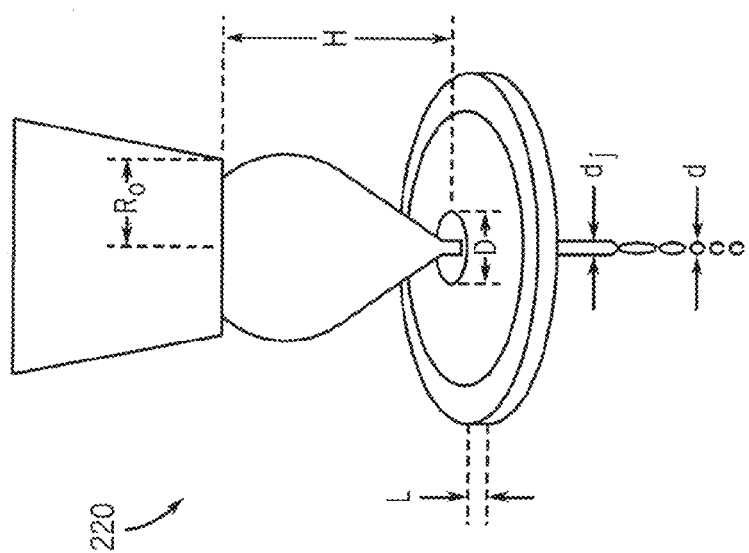

- COMBINATION A
- COMBINATION B
- COMBINATION C
- COMBINATION D

- SMPS
- NICOMP 380ZLS

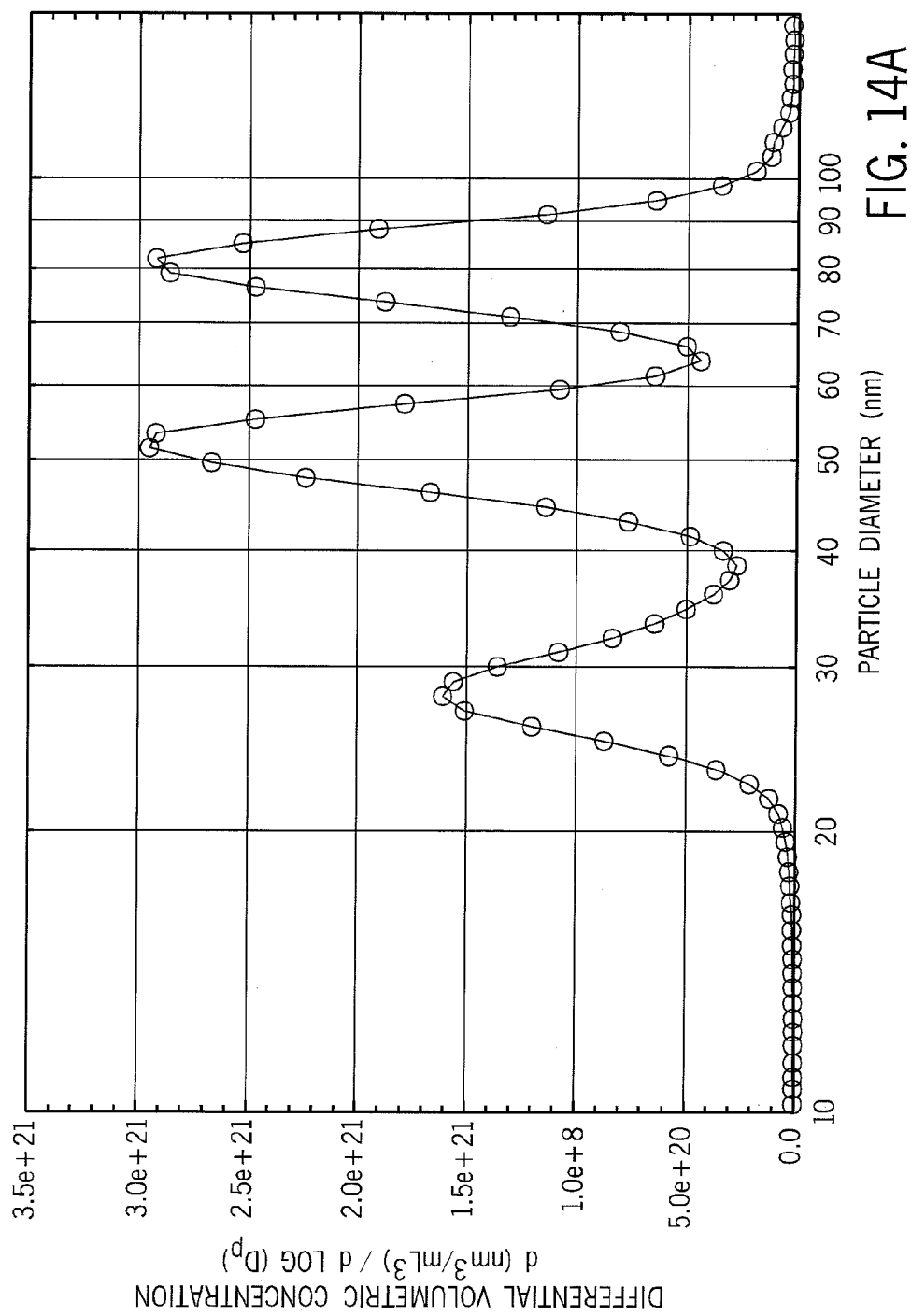

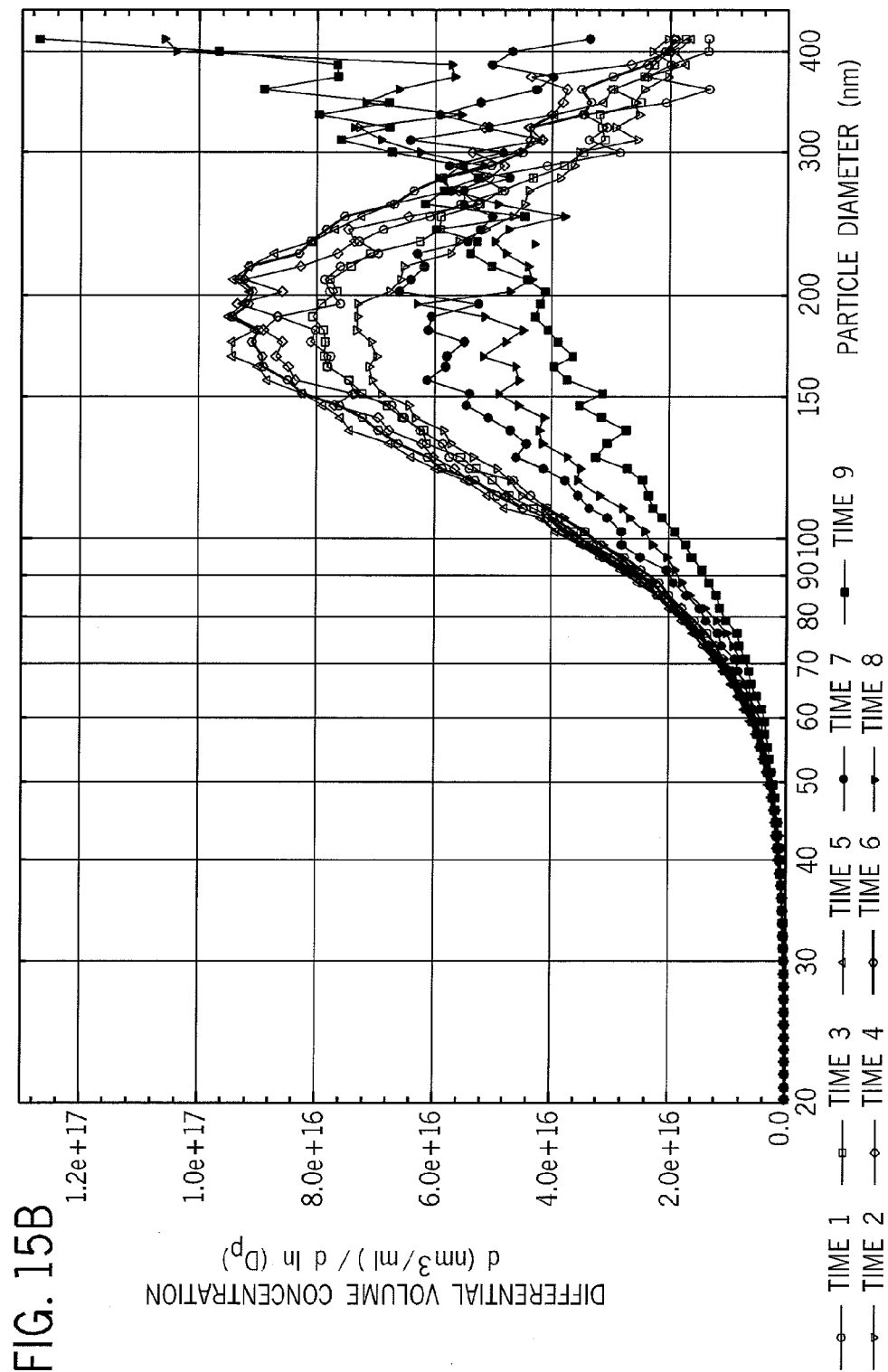

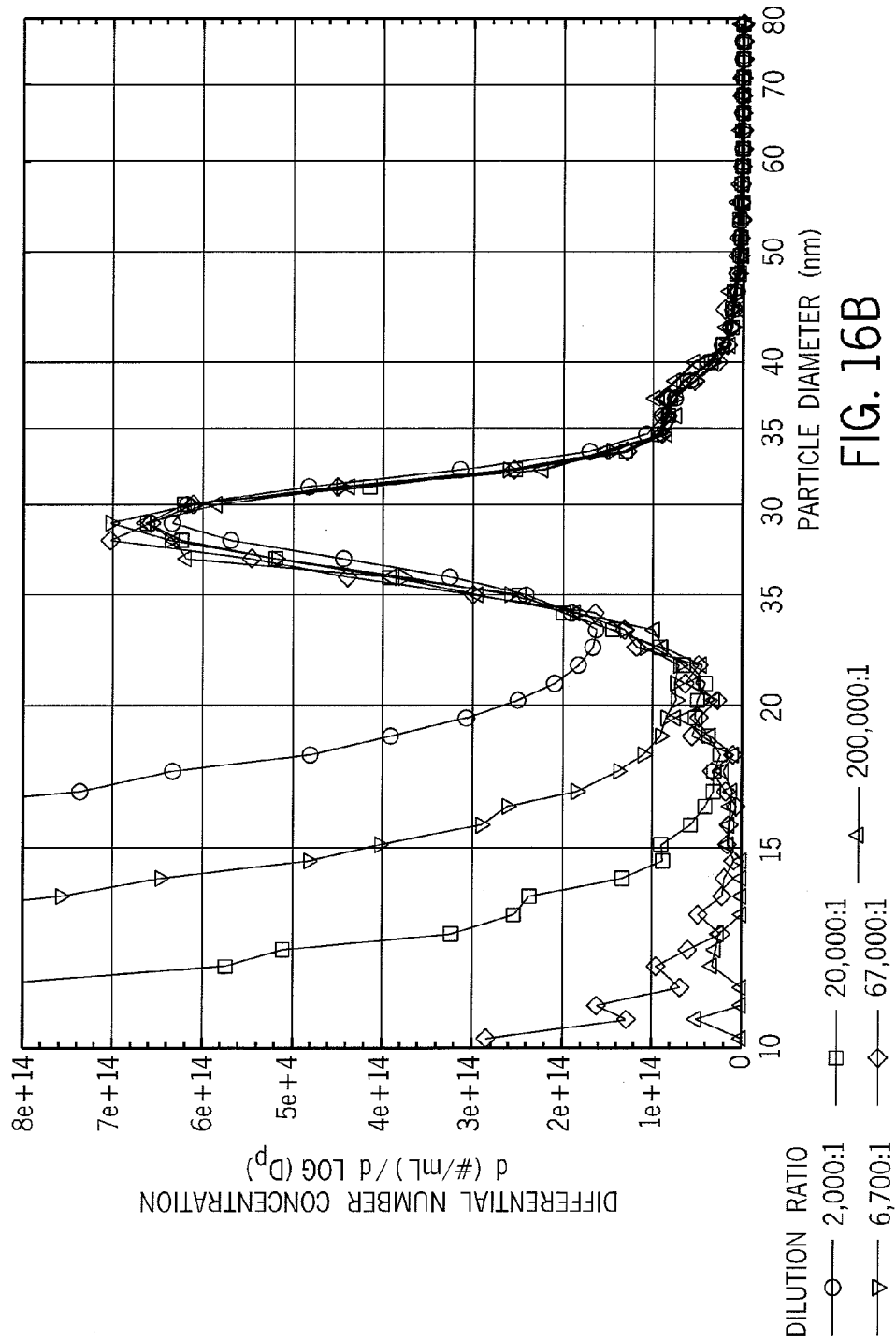

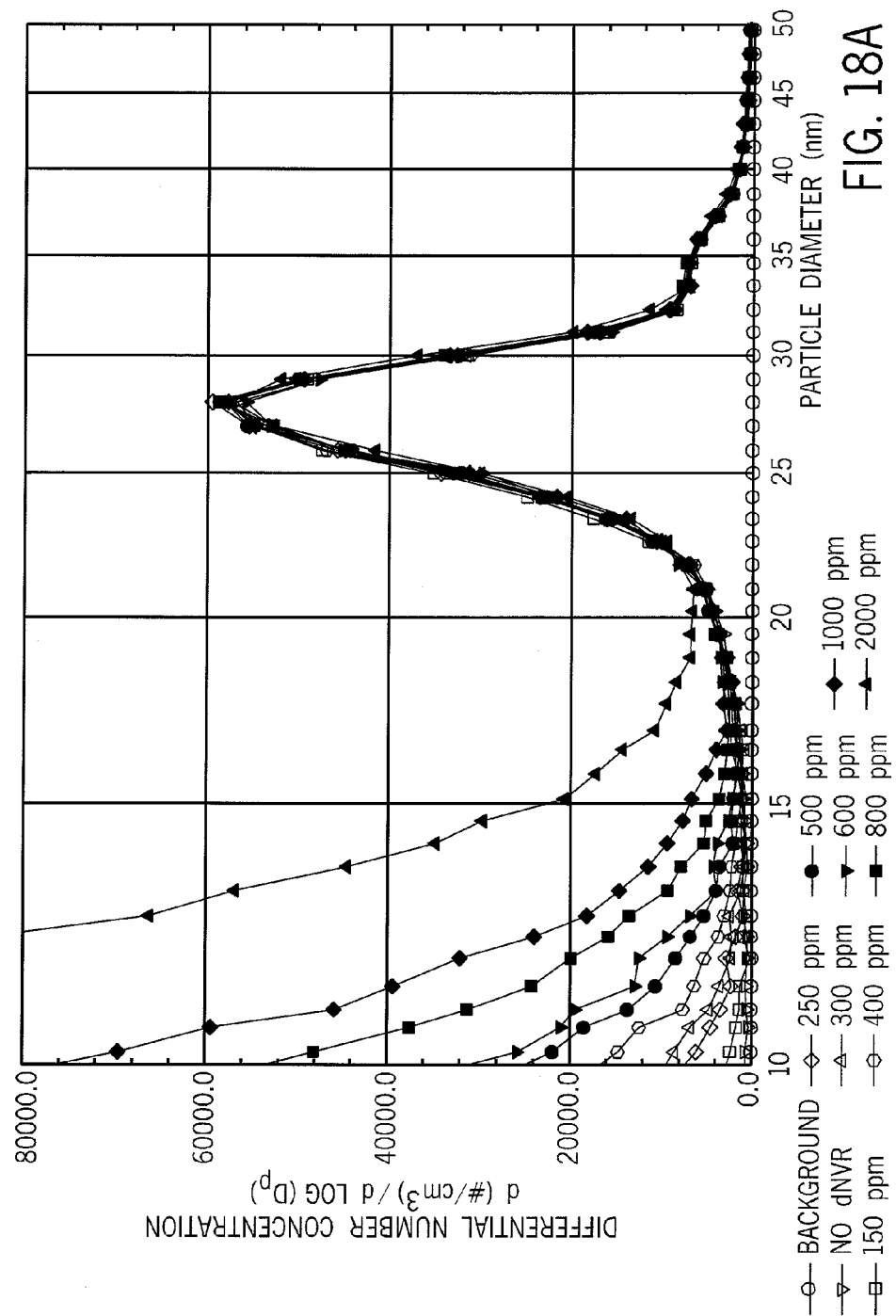

RESIDUE CONCENTRATION MEASUREMENT TECHNOLOGY

CROSS-REFERENCE TO RELATED APPLICATIONS, IF ANY

This application is a continuation in part of co-pending U.S. patent application Ser. No. 12/357,088, filed Jan. 21, 2009 now U.S. Pat. No. 8,272,253, which claims the benefit under 35 U.S.C. §119(e) of co-pending U.S. Provisional Patent Application Ser. No. 61/011,901, filed Jan. 22, 2008, which is hereby incorporated by reference.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND

1. Field

The present invention relates, generally, to analysis methods and apparatus for use with compositions of matter. More particularly, the invention relates to a method and apparatus for measuring the size and concentration of small particles and the concentration of dissolved, non-volatile residues in colloidal suspensions. Most particularly, the invention relates to an apparatus and method for separating dissolved and particulate residues in a colloidal suspension to determine both the size distribution and concentration of the particulate species (i.e. insoluble particles) and the concentration of dissolved non-volatile residue. The technology is useful, for example, for accurate measurement of particle size distributions and dissolved non-volatile content in colloidal suspensions. The invention is suitable for use in the semiconductor device manufacturing industry, the ink manufacturing industry, and in other fields.

2. Background Information

The invention provides methods and apparatus for measurement of Particle Size Distributions (PSDs) and concentration of particulate Non-Volatile Residue (hereinafter "pNVR") and the concentration of dissolved Non-Volatile Residue (hereinafter "dNVR") in colloidal suspensions. There are numerous applications in which the PSD and dNVR concentrations in colloidal suspensions are important in determining the efficacy of the suspension. Examples include slurries used in chemical mechanical planarization (CMP) of silicon wafers, as well as wafers composed of other materials, during semiconductor chip manufacturing and pigment-based inks. The PSD and dNVR content of CMP slurries determines the planarization rate, surface smoothness and scratch density on the wafer surface following the CMP process. All of these are important in determining the finished semiconductor device yield and performance. The size distribution of pigment inks is important in determining color development while dNVR content is important in determining rheological properties and stability of the inks.

Historically, technologies have been developed to measure "total" non-volatile residue ("dissolved" residue plus "particulate" residue) or to measure the particle size distribution in colloidal suspension. Techniques to separate and measure the two components of residue simultaneously have not been developed insofar as is known prior to the present invention.

Total NVR (tNVR) has typically been measured using non-volatile residue monitors (NVRM or NRM). These instruments work by forming an aerosol of the liquid, evaporating the liquid in the aerosol and measuring the number of particles in the aerosol. The instruments measure combined dNVR and pNVR and are typically used to measure the tNVR content in liquids that contain mostly dNVR (little pNVR present). They have been used to measure filter retention of colloidal silica particles; however, measurement accuracy was compromised by interference caused by dNVR.

Measurement of particle size distributions in colloidal suspensions, has typically been addressed using dynamic light scattering (DLS), laser diffraction (fraunhofer diffraction) or centrifugal sedimentation. These methods only measure relative PSDs. Insofar as is presently known, they cannot determine actual concentrations.

PSDs in colloidal suspensions have also been analyzed using a combination of electrospray and mass spectroscopy. Electrospray is used to generate small droplets by subjecting the liquid to a high electric field. The liquid must be moderately conductive and the droplets become highly charged during formation. High purity liquids typically have low conductivity making the formation of small droplets difficult. Also, the high charge on the particles can result in particle agglomeration and may cause other changes in particle properties. The agglomeration issue can be addressed by exposing the aerosol to ionizing radiation.

For these and other reasons, a need exists for the present invention.

All US patents and patent applications, and all other published documents mentioned anywhere in this application are hereby incorporated by reference in their entirety.

BRIEF SUMMARY

The present invention provides methods and apparatus for (a) separating dNVR and pNVR in a colloidal suspension, (b) measuring the concentration of dNVR in the suspension, (c) measuring the concentration of pNVR particles larger than 5 nm in diameter or smaller in the suspension, and (d) measuring the size distributions of such pNVR particles. The method and apparatus are practical, reliable, accurate and efficient, and are believed to fulfill a need and to constitute an improvement over the background technology.

In one aspect of the present invention, a method includes the steps of, providing a specimen of a colloidal suspension to be tested, isolating small, uniformly sized droplets from the specimen, evaporating the droplets to dryness, and counting and sizing the resulting particles. Two types of particles result from the isolation/evaporation process: (a) those from droplets that originally contained pNVR and (b) those from droplets that contained only dNVR. The pNVR-free droplets form small particles consisting of dNVR when the volatile liquid is removed. If the droplets are sufficiently small and uniformly sized, each droplet will contain either 0 or 1 particulate species and the particles formed from dNVR will be significantly smaller than the particulate (pNVR) species. By measuring the resulting PSD both the concentration of the dNVR (very small particles) and the PSD of the pNVR (larger particles) can be measured.

In another aspect of the present invention, an apparatus includes a Nebulizer/Impactor and a Scanning Mobility Particle Sizers (SMPS). The Nebulizer/Impactor has means to form or form and isolate small, uniformly sized droplets from a colloidal suspension. The SMPS accurately sizes and counts particles present after the small, uniformly sized droplets are dried to measure the PSD and concentration of the pNVR and the concentration of the dNVR.

A Nebulizer/Impactor combination is provided for generating an aerosol composed of multiple droplets of a colloidal suspension. The Nebulizer-Impactor includes a housing forming a mixing chamber having (i) a liquid entrance for receiving a sample liquid into the chamber, (ii) a primary orifice having a first diameter for receiving a pressurized gas into the chamber for merger with the sample liquid to generate an aerosol composed of multiple droplets of the sample liquid suspended in the gas, and (iii) a secondary orifice having a secondary diameter for conducting the aerosol out of the chamber. The second orifice is less than a major dimension of the mixing chamber taken in a direction substantially perpendicular to an axis of the secondary orifice, so as to restrict flow out of the mixing chamber to generate a back pressure in opposition to entry of the sample liquid and the pressurized gas into the chamber.

In contrast to other nebulizers in which the chamber exit is simply open to the downstream components with a diameter equal to that of the chamber, the exit orifice in the nebulizer has a diameter less than that of the chamber, more preferably less than half the diameter chamber. The diameter reduction provides a constriction that produces a higher kinetic energy mixing of the gas and liquid in the merger zone. As a result, the nebulizer generates smaller droplets. The secondary orifice also helps direct the aerosol toward the impactor surface raising the impactor efficiency.

Another factor reducing the droplet size produced by the atomizer/impactor is close axial positioning of an impactor just downstream of the secondary orifice. The more closely spaced impactor removes a greater proportion of the larger droplets.

In a preferred version of nebulizer/impactor, the impactor axial spacing from the secondary orifice is adjustable through movement of the impactor. For example, a threaded mounting of the impactor to the nebulizer frame allows axial position adjustment by turning the impactor about its longitudinal axis. The average size of the droplets in the aerosol leaving the nebulizer can be increased or decreased by respectively enlarging or reducing the axial spacing between the secondary orifice and the impactor. The average size can also be decreased and the uniformity increased by making the shape of the housing containing the secondary orifice conformal to the impactor shape.

The droplet size produced by atomizer/impactor also can be adjusted by changing or selecting the secondary orifice. Reducing the diameter of the secondary orifice is believed to increase back pressure and reduce droplet size. It has been found useful to provide a secondary orifice with a diameter larger than that of the primary orifice. The ratio of the secondary orifice diameter to the primary orifice diameter can range from slightly above one, to about two in versions that incorporate a secondary orifice.

The aspects, features, advantages, benefits and objects of the invention will become clear to those skilled in the art by reference to the following description, claims and drawings.

BRIEF DESCRIPTION OF THE SEVERAL VIEWS OF THE DRAWING

The present invention, and the manner and process of making and using it, will be better understood by those skilled in the art by reference to the following drawings.

FIG. 1 is a flow diagram of one embodiment of the method of the present invention.

FIG. 2A is a diagram illustrating an embodiment of the apparatus of the present invention.

FIG. 2B is a diagram illustrating an alternative embodiment of the apparatus of the invention.

FIG. 4 is a crossectional view of an embodiment of a plate impactor component which is used in an embodiment of the apparatus of the invention.

FIG. 5 is a crossectional view of an embodiment of a virtual impactor which is used in another embodiment of the apparatus of the invention.

FIG. 14A shows pNVR particle size distributions in Colloidal Dispersion A measured using Combination D apparatus of FIG. 12 with an SMPS detector.

FIG. 15B shows the change in slurry volume-weighted PSD over time during handling as measured using Combination D apparatus with an SMPS analyzer via a graph of differential volume concentration versus particle diameter.

FIG. 16B shows particle concentration measurements of a liquid containing 0.1% by weigh pNVR silica particles and 1% by weight dNVR following different dilution ratios.

FIG. 18A shows particle concentration measurements of a liquid containing pNVR silica particles and different concentrations of dNVR.

DETAILED DESCRIPTION

Figure 2C:
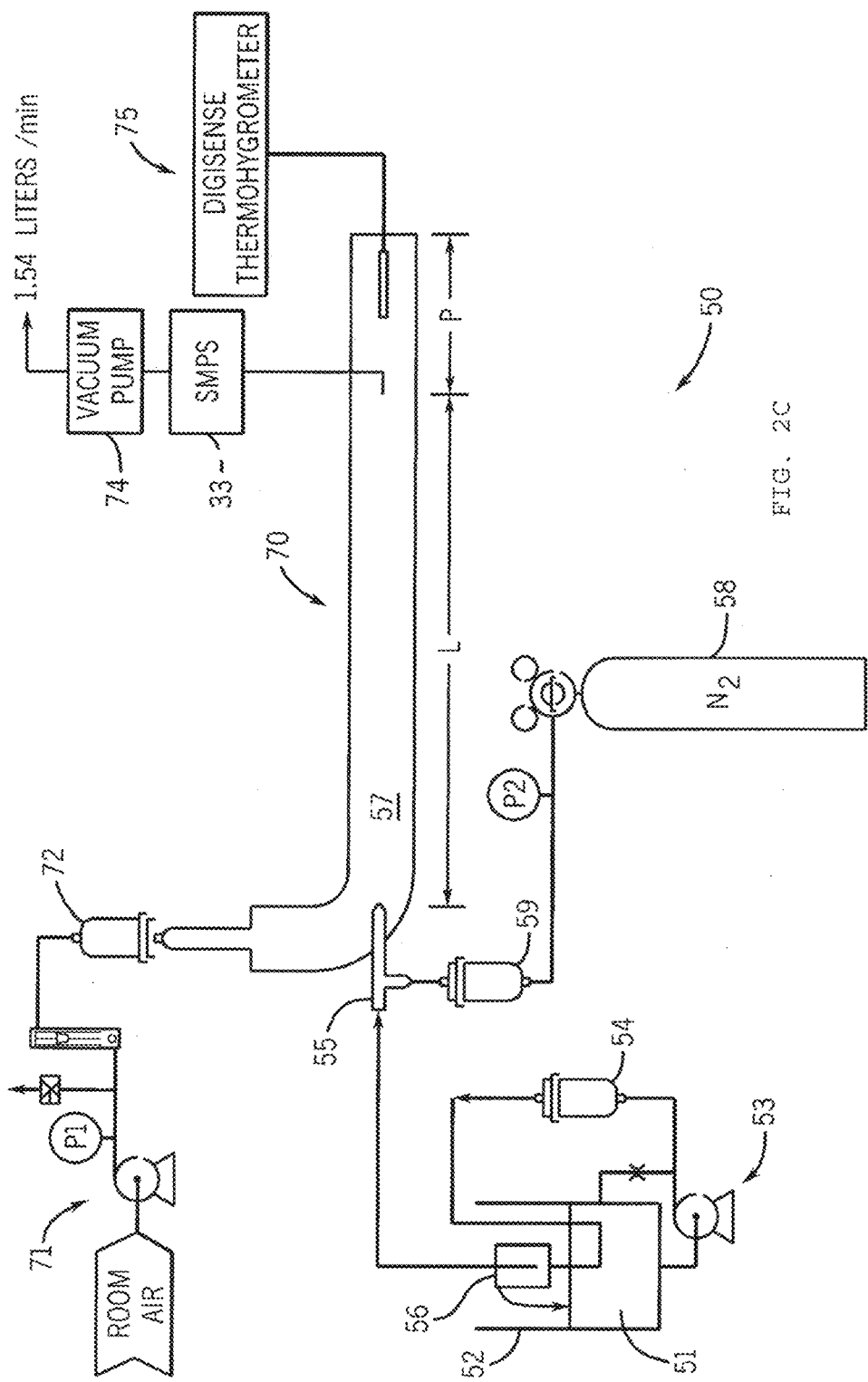
FIG. 2C illustrates a system for measuring droplet size distributions produced by droplet formers.

The present invention provides a method and apparatus for determining the concentration of dissolved non-volatile residue (dNVR) and the size distribution and concentration of particulate non-volatile residue (pNVR) in a colloidal suspension.

A. Methods of the Invention.

The method involves several aspects including (a) forming droplets, for example via aerosolization, from a sample of a colloidal suspension to be analyzed, (b) isolating small droplets from the droplets, for example less than 1 um in size, (c) drying the droplets to remove the liquid, for example via evaporation, and (d) counting and sizing the residual particles.

Importantly, the aerosol droplets isolated are small and uniformly sized, less than 1 μm and preferably a median size less than 0.5 μm. The droplets must be small and uniformly sized because dNVR in the droplet will form a "residue" particle as a result of drying. If the droplets are sufficiently small and uniformly sized, the particles formed from the dNVR following evaporation will be significantly smaller than the particles initially in the liquid. In addition, small droplets are less likely to hold multiple particulate species that would be counted as one in the subsequent analysis.

The size of a residue particle resulting from evaporation of a liquid droplet containing no pNVR can be determined from the concentration of the dNVR in the droplet using equation 1 where $d_s$ is the size of the final residue particle, $d_d$ is the size of the droplet diameter and $F_v$ is the volume fraction of non-volatile residue in the droplet:

$$d_s = d_d(F_v)^{1/3} \quad (1)$$

If the density of the non-volatile residue in the droplet is the same as the liquid (1.0 g/cm$^3$ in the case of water), then $F_v$ is simply the weight concentration of non-volatile residue (C). If the water has a non-volatile concentration of 1 ppm with a density of 1.0, equation 1 above can be used to calculate the size of a dNVR particle resulting from evaporating a 0.3 μm (300 nm) droplet, as follows:

$$d_s = d_d(C)^{1/3} = 300 \text{ nm}(10^{-6})^{1/3} = 300 \text{ nm}(0.01) = 3 \text{ nm} \quad (2)$$

Hence, if the particles in the colloidal suspension are all larger than 10 nm, the 3 nm particles resulting from dNVR will be <⅓ the size of the smallest pNVR particles.

The small, uniformly sized droplets required by the present invention may be generated by firstly making droplets of diverse sizes and secondly removing large droplets. Alternatively, the desired droplets may be made in a single step. An example of the former embodiment of the method is implemented by generating droplets by a compressed air nebulizer or an ultrasonic nebulizer and then removing large droplets by directing them to an impaction surface such as a plate impactor or a virtual impactor. An example of generating small, uniform droplets directly is by way of a vibrating orifice aerosol generator. After the droplets are formed, liquid in the droplets is removed before the droplets collide or coalesce. Liquid removal may be accomplished by heating to dry via dilution air, heated air, or heating the liquid. It may also be accomplished by evaporation. And after drying to isolate the particles, the particles are counted and sized by optical particle counters (OPC), scanning mobility particle sizers (SMPS) or other instruments.

Thus, referring to FIG. 1, a flow chart of a basic embodiment of the method 10 of the invention involves the steps of, providing 11 a liquid sample, forming 12 very small, uniformly sized droplets, via an aerosol, from the liquid sample to be analyzed, drying 13, for example via evaporating, the droplets in the aerosol, and counting and sizing 14 the residual particles. Variants of this embodiment of the method are discussed above.

B. Apparatus of the Invention.

Referring to FIG. 2A, one embodiment of the apparatus 20 of the present invention comprises means 22 for forming droplets of diverse sizes connected to a sample input 21. Means 23 for removing large droplets is communicatively connected to the means 22 for forming droplets An example of droplet former 22 is a compressed air nebulizer, an ultrasonic nebulizer, or a flow-focusing nebulizer examples of which are shown in FIG. 3A-C. An example of means 23 for isolating small uniformly sized droplets is a plate impactor or a virtual impactor (examples of which are shown in FIGS. 4 and 5) having an impaction surface at which an aerosol stream output by the nebulizer 22 is directed and which removes large droplets. After the desired droplets are formed, liquid in the droplets is removed before the droplets collide or coalesce by liquid removal means 24. Examples of such means include a stream of dilution air, heated air, or a liquid heater. Drying may also be accomplished by a fast evaporator. A particle analyzer 25 is communicatively connected to the liquid remover 24. Examples of such analyzer for counting and sizing includes an OPC, SMPS or other instrument or combination of instruments. Exemplary nebulizers, impactors and analyzers are described in detail below.

Referring to FIG. 2B, another embodiment of the apparatus 30 of the present invention comprises means 32 for making droplets of a small and uniform size connected to a sample input 31. An example of such means is a vibrating orifice aerosol generator, an example of which is described in detail below. After the desired droplets are formed, liquid in the droplets is removed before the droplets collide or coalesce by liquid removal means 33. Examples of such means include a stream of dilution air, heated air, or a liquid heater. Drying may also be accomplished by a fast evaporator. A particle analyzer 34 is communicatively connected to the liquid remover 33. Examples of such analyzer for counting and sizing includes an OPC, SMPS or other instrument or combination of instruments.

Figure 3A:
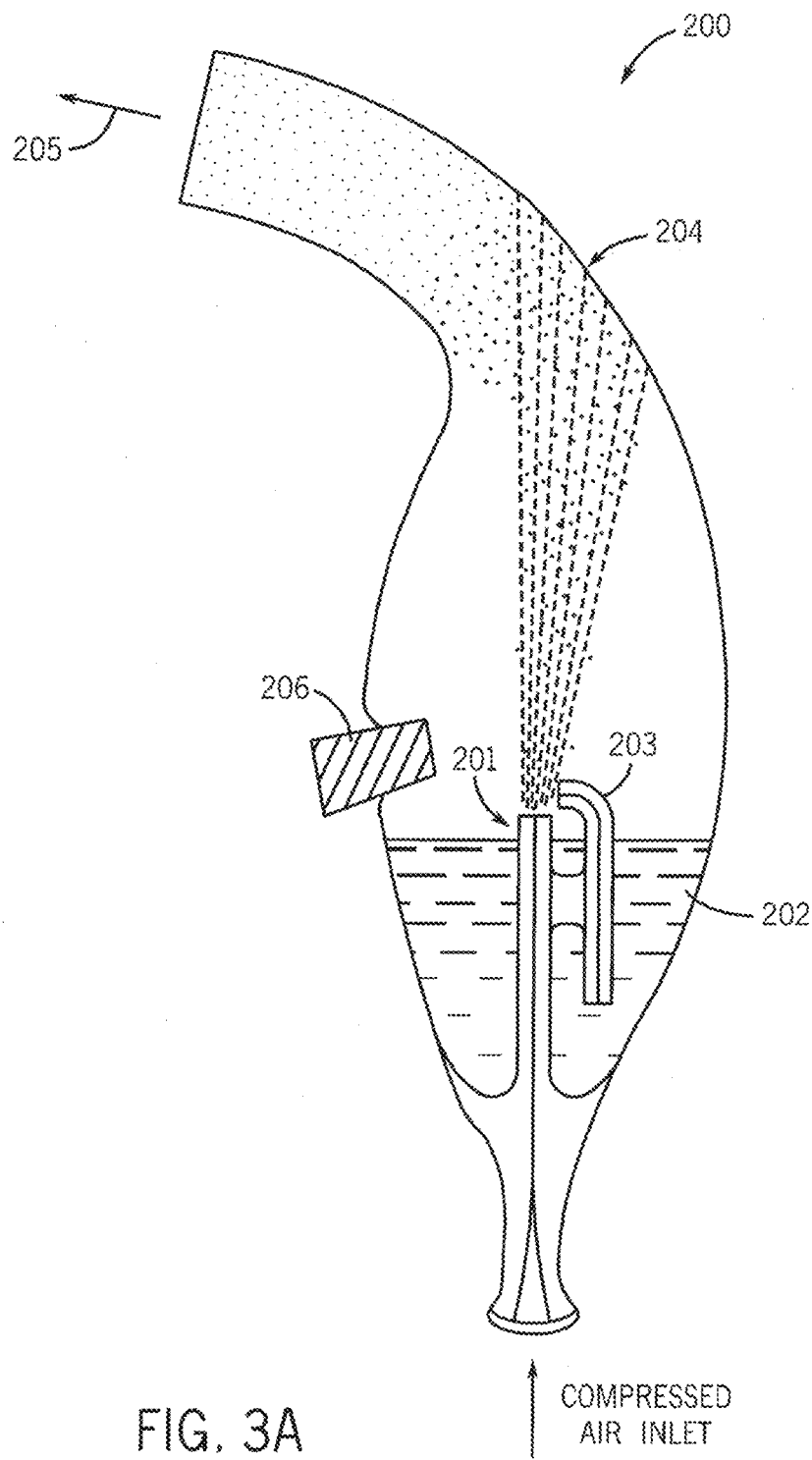
FIGS. 3 A-C illustrate pneumatic, concentric and flow focusing embodiments of a nebulizer component of the apparatus of the invention.
Figure 3B:
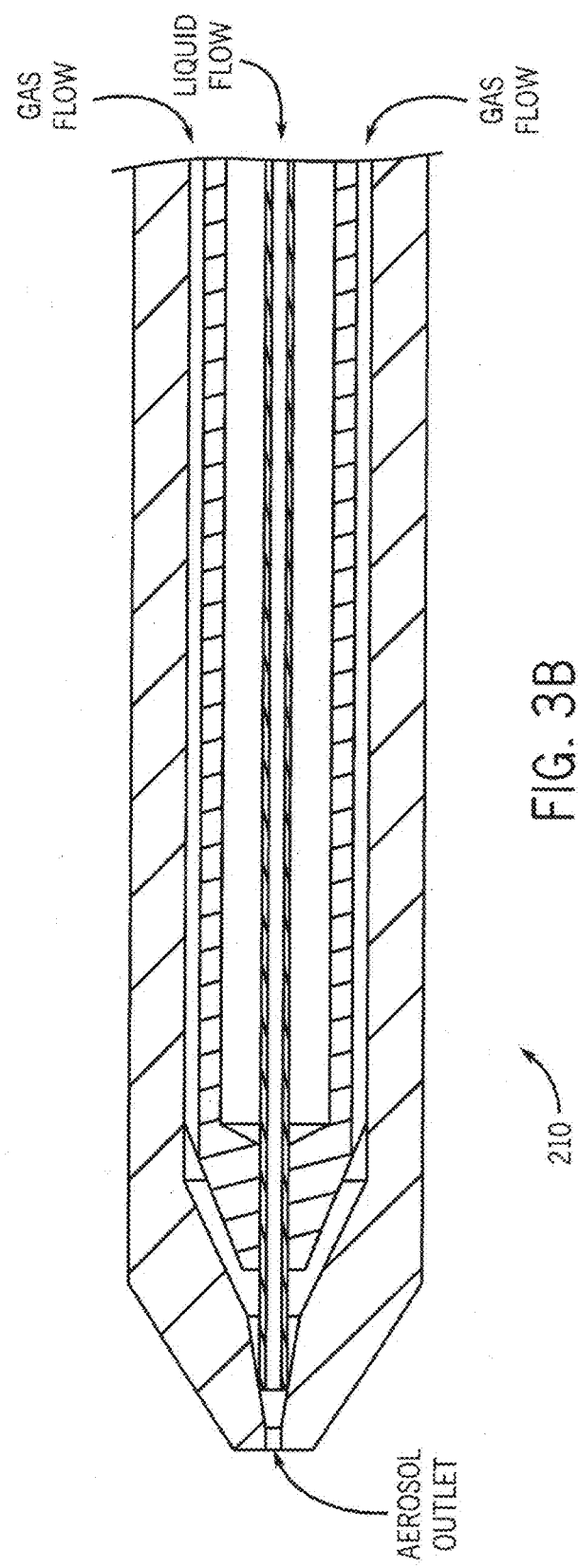

An apparatus for counting and sizing droplets formed by the droplet forming methods is shown in FIG. 2C. A test solution 51 is input to a vessel 52. Solution 51 is output via a gear pump 53 through a filter 54 and into a small overflow vessel 56. Most of the liquid input to vessel 56 returns to vessel 52. A small portion of the liquid is sent to droplet former 55. Droplet former 55 forms an aerosol 57 containing small droplets. The nebulizer 55 is connected to a pressurized gas source 58, preferably compressed air or $N_2$. The gas is filtered, for example via a Wafergard® filter 59. Various droplet former 55 embodiments are discussed below.

The aerosol 57 is input by the droplet former 55 to a drying chamber 70. The drying chamber 70 is an elongated structure with input and output ends, a predetermined length and a predetermined horizontal dimension. The drying chamber 70 input end is connected to a source of room air via a pump 71. Air is preferably filtered, for example via a Millipore 0.22 micron Hydrophobic Millipak® filter 72. The droplet former 55 is disposed at a predetermined location on the drying chamber 55. A Scanning Mobility Particle Sizer (SMPS) 33 is disposed at a predetermined location on the drying chamber 55 a predetermined distance "L" from the nebulizer 55. A vacuum pump 74 is connected to the SMPS 33. The pump 74 operates at about 1.54 liters per minute. A thermohygrometer 75, for example a DigiSense meter is disposed at the output end of the drying chamber 70, a predetermined distance "1'" further downstream from the SMPS 33.

Referring to FIG. 3A, an example pneumatic nebulizer 200 which may be used to create initial droplets is disclosed. In a typical pneumatic nebulizer 200 with vent 206, compressed air exits from a small orifice 201 at high velocity creating a low pressure in the exit region. The low pressure causes liquid to be drawn into the airstream from a second tube 203 from liquid reservoir 202. The high velocity air causes the liquid to accelerate and break into droplets. The high velocity spray 204 is directed toward an impaction surface where the largest droplets are removed and an aerosol 205 is output.

Commercially available nebulizers typically generate aerosols with droplets whose size is log-normally distributed. Median droplet sizes are typically 0.5-5.0 µm. The geometric standard deviation is typically ~2.0. The large geometric standard deviation means that the nebulizers generate a significant number of large droplets. For example, approximately 0.0003% of the droplets from a nebulizer producing an aerosol with a median droplet size of 1.0 µm and geometric standard deviation of 2.0 would be larger than 25 µm. This is in an unacceptable number of large droplets for the applications described above. Examples of commercially available pneumatic nebulizers include Laskin nebulizer, Babington nebulizer, Cross-flow nebulizer, and Pre-filming nebulizer. Referring to FIGS. 3B and 3C, known concentric 210 and flow focusing pneumatic 220 nebulizers might also be used. Ultrasonic generators are also useable for generating small droplets, but less preferred than nebulizers.

As was discussed above, large droplets can be removed from the aerosol using either a plate impactor 300, shown in FIG. 4, or a virtual impactor 350 as shown in FIG. 5. In the plate impactor, the plate deflects the aerosol flow to follow an abrupt 90° bend. Droplets with sufficient inertia deviate from the flow stream, impact on the plate, and are removed from the gas stream. A virtual impactor is similar to a plate impactor except that the droplets are impacted into a quiescent region where they are withdrawn from the aerosol by a small secondary flow.

The effectiveness of impactors for removing particles is related to the Stokes number or impaction parameter. The Stokes number ($S_{tk}$) is proportional to the square of the droplet size as shown in equation 3 where $\rho_p$ is the droplet density, U is the nozzle velocity, $\eta$ is the gas viscosity, and $D_j$ is the nozzle diameter.

$$S_{tk}=(\rho_p d_p^2 U)/(9\eta D_j) \quad (3)$$

Figure 6:
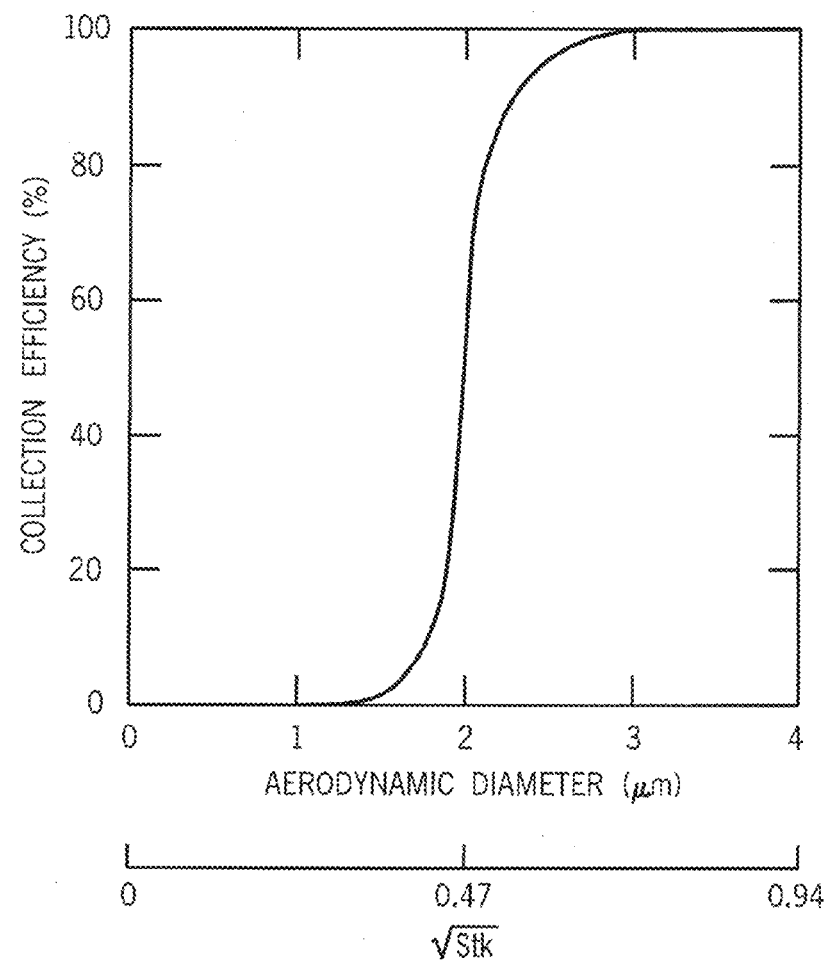
FIG. 6 is a diagram showing impactor efficiency.

Impactors can be designed with sharp efficiency curves. An impactor designed to remove 50% of the droplets >10 µm should remove virtually all droplets >25 µm. An example of a typical impactor efficiency curve is shown in FIG. 6.

Figure 7:
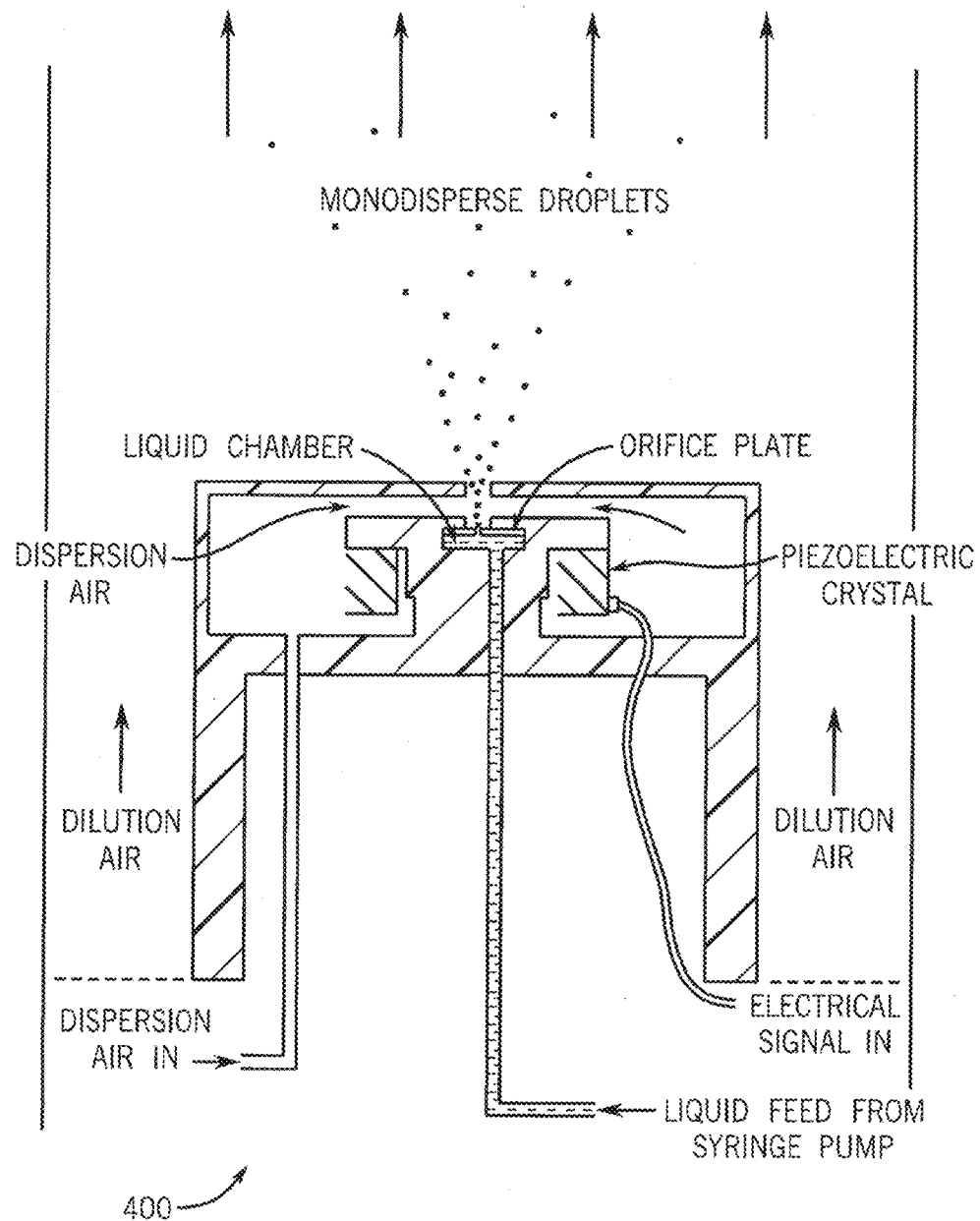
FIG. 7 illustrates an embodiment of a vibrating orifice generator used in an embodiment of the apparatus of the invention.

Another approach to generating an aerosol with small droplets is through the use of a vibrating orifice aerosol generator 400. Referring to FIG. 7, these generators 400 work by vibrating a liquid at a high frequency as it passes through a small orifice. They produce nearly monodisperse droplets. The size of the droplets generated can be calculated using equation 4 where $Q_L$ is the liquid flow rate and f is the oscillating frequency:

$$d_d=(6Q_L/\pi f)^{1/3} \quad (4)$$

A generator operating at 2 MHz with a flow rate of 0.02 ml/min would produce 10 µm droplets.

Figure 8:
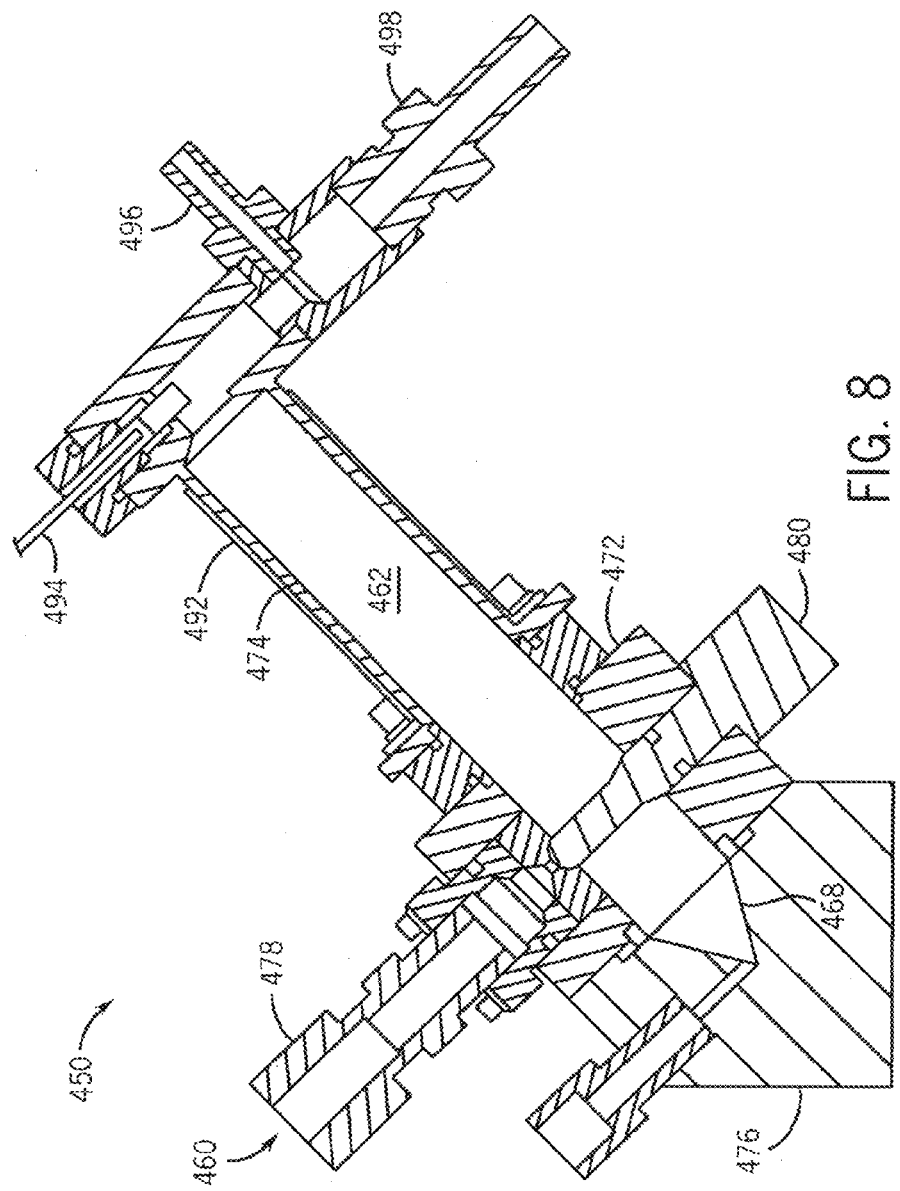
FIG. 8 is a sectional side elevation view of an embodiment of the system of the present invention including a combination nebulizer-impactor.
Figure 9:
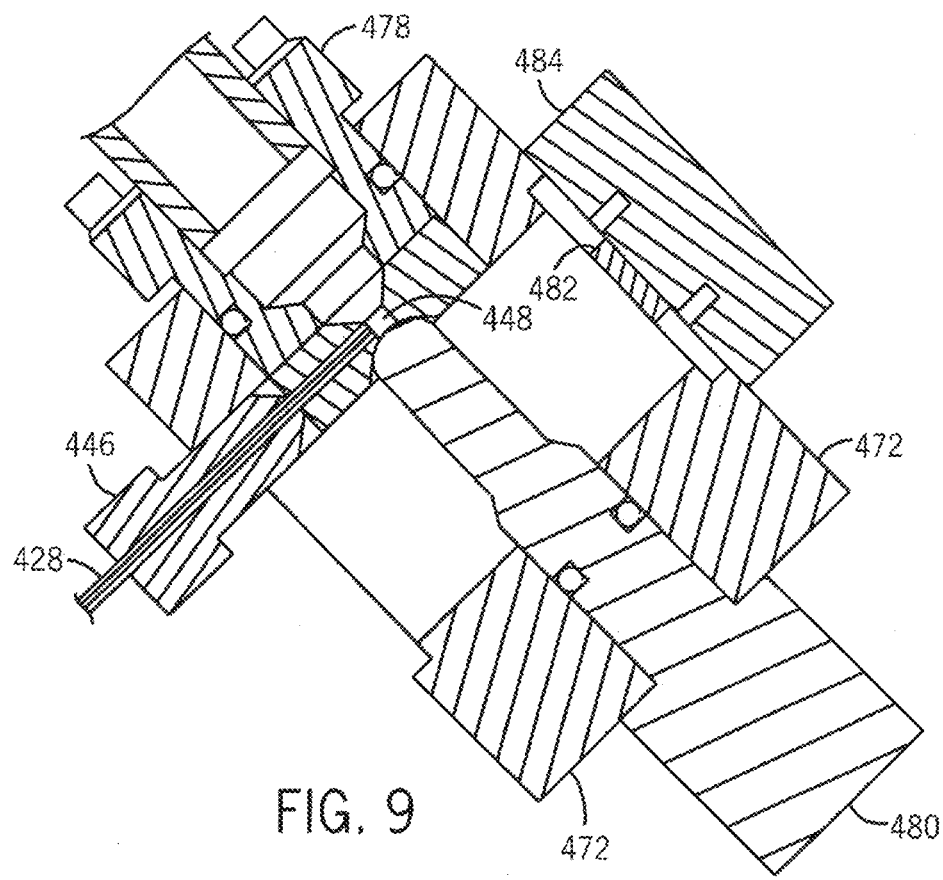
FIG. 9 is a sectional view of the combination nebulizer-impactor.
Figure 10:
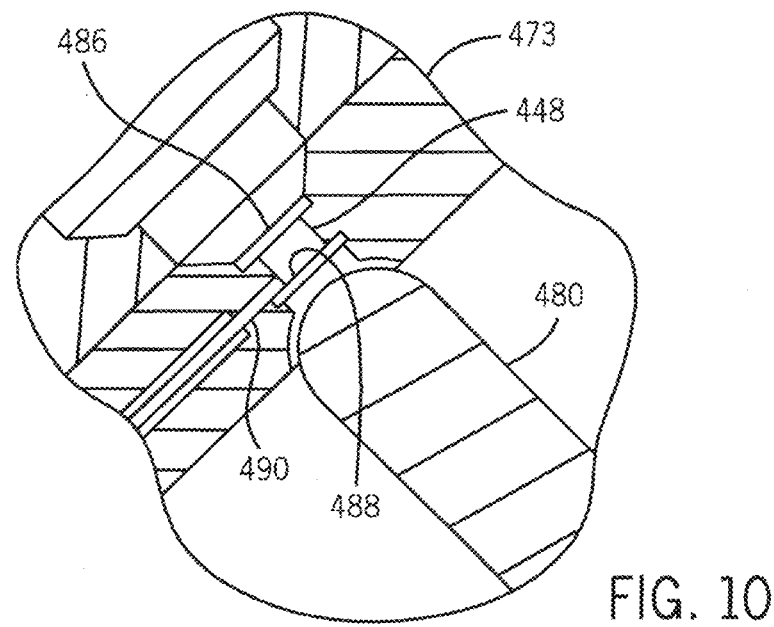
FIG. 10 is an enlarged view showing a portion of the nebulizer-impactor of FIGS. 8 and 9.

A preferred approach involves a system including a combination nebulizer-impactor 450. Referring to FIGS. 8-10, an input conduit 428 transfers fluid to a pneumatic nebulizer portion of the system. The nebulizer 450 also receives air, nitrogen or another gas under pressure from a pressurized gas source through conduit 460. Within nebulizer 450, the liquid sample and compressed gas are merged to generate an aerosol including droplets of the liquid sample suspended in the gas.

Nebulizer 450 includes a reservoir 468 in fluid communication with the merger zone. The reservoir 468 collects most of the liquid supplied through the input conduit 428, i.e. the liquid not used to form the aerosol droplets.

The inclined orientation shown is advantageous for liquid drainage and evacuation, although not critical. A housing of the nebulizer 450 has several integrally coupled sections, including a stainless steel housing section 472 that encloses merger zone 448, a steel housing section 474 forming the aerosol conditioning zone, and a housing section 476 providing the reservoir 468. Housing section 472 supports a fitting 478 for receiving the air or other compressed gas from conduit 460. This housing section 472 also supports an impactor 480, through a threaded engagement that permits adjustment of the axial spacing between impactor 480 and merger zone 448.

With reference to FIG. 9, housing section 472 further supports a thermoelectric device 482 that functions to maintain a stable temperature of about 30.degree. C. in the vicinity of merger zone 448. More particularly, the thermoelectric device 482 extracts heat from housing section 472 and transfers it to a heat sink 484. The thermoelectric device 482 also may function as a heater for the nebulizer. The constant temperature promotes consistent droplet formation. Housing section 472 further supports bulkhead fitting 446, which secures an input conduit 428 used to transfer the sample liquid to merger zone 448.

As best seen in FIG. 10, merger zone 448 takes the form of a cylindrical chamber in a Teflon orifice housing 473. A sapphire orifice plate 486 defines an entrance or primary orifice to receive pressurized gas into the chamber from conduit 460. A sapphire orifice plate 488 defines an exit or secondary orifice through which the merged liquid and gas leave the chamber. In addition, a liquid receiving entrance 490 conducts the sample liquid into the chamber.

In one suitable version of nebulizer 450, primary orifice 486 has a diameter of 0.006 inches, and secondary orifice 488 has a diameter of 0.008 inches. The chamber 448 has a diameter of 0.020 inches, and an axial length, i.e. space in between orifice plates 486 and 488, of 0.020 inches.

More generally, the secondary orifice 488 diameter is larger than the primary orifice 486 diameter, yet less than the diameter of the cylindrical chamber 448. As compared to prior devices in which there is no secondary orifice 488 and the chamber is simply open at the exit end, there is a back pressure due to the secondary orifice which increases the feed pressure to the merger zone 448 and results in a higher kinetic energy mixing of the liquid and compressed gas. This advantageously results in smaller sample liquid droplets in the aerosol leaving the merger zone 448.

As the size of the secondary orifice 488 is reduced, the droplet size is reduced and the back pressure is increased. When the sample liquid is water, it has been found satisfactory to form the secondary orifice 488 and the primary orifice 486 at a diameter ratio of 2 to 1 as indicated by the diameters given above. For a sample liquid with a boiling point lower than water, the preferred diameter ratio is closer to 1, yet the secondary orifice 488 remains larger than the primary orifice 486.

The higher energy in the merger zone 448 more effectively breaks up the liquid. The secondary orifice 488 also appears to improve the efficiency of the impactor 480 downstream. The ratios of primary 486 and secondary 488 orifice diameters can be selected to vary the pressure at the liquid entrance to the merger zone, relative to atmospheric pressure. Depending on the diameter ratio, air inlet pressure and liquid flow rate the liquid pressure can be adjusted from below atmospheric pressure to a pressure nearly equal to the inlet air pressure.

As seen in FIG. 10, impactor 480 is disposed coaxially with merger zone 448, spaced apart in the axial direction from orifice plate 488. The impactor 480 cooperates with housing section 472 to form a thin, somewhat hemispherical path to accommodate the flow of air and droplets beyond the merger zone 448. The smaller droplets tend to follow the air flow, while the larger droplets tend to collide with impactor 480 and are removed from the aerosol stream. Thus, the aerosol moving into conditioning zone 462, upwardly and to the right as viewed in FIG. 8, includes only those droplets below a size threshold determined largely by the axial spacing between secondary orifice 488 and impactor 480. The size threshold is increased by increasing the axial spacing, and reduced by moving the impactor 480 closer to orifice plate 488.

The droplets impinging upon impactor 480 may remain on the impactor 480 momentarily, but eventually descend to reservoir 468 then drain from the nebulizer 450. If desired, impactor 480 may be formed of sintered metal to provide a porous structure that more effectively prevents the larger, impacting droplets from interfering with the aerosol flow.

A secondary gas may be introduced into nebulizer 450 at a location upstream of the nebulization region. The secondary gas sweeps dead space in the nebulization region resulting in a faster response, reduced axial diffusion, and less smearing of the output due to mixing.

As was discussed above in general, once the aerosol is formed, the liquid in the droplets must be evaporated before the droplets have a chance to collide and coalesce. Drying can be accomplished using dilution air, heated air or heating the liquid.

Once the liquid is evaporated, the particles in the aerosol can be counted and sized by a number of techniques including, but not limited to Optical Particle Counters (OPCs), and Scanning Mobility Particle Sizers (SMPS). OPCs are similar to those used in liquids. They size and count individual particles as they pass through a laser beam. Examples of OPCs include those made by Particle Measuring Systems, RION, Horiba, Particle Sizing Systems, and Hach Ultra.

In summary, the preferred embodiment of the apparatus of the invention includes the Nebulizer/Impactor 450 and a Scanning Mobility Particle Sizer (SMPS). This embodiment is believed to be best suited for measurement of dNVR concentration and pNVR PSD.

Although the apparatus and method of the invention has been described in connection with the field of semiconductor device manufacture, it can readily be appreciated that it is not limited solely to such field, and can be used in other fields.

Figure 11:
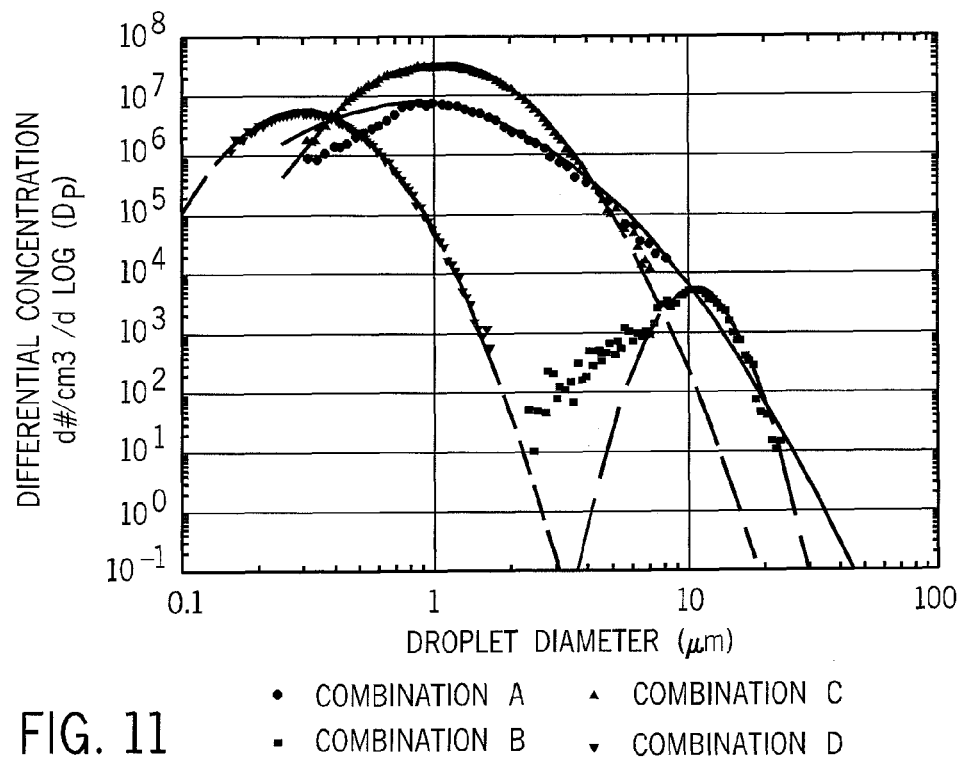
FIG. 11 is a graph of droplet size distributions produced by various combinations A, B, C and D of nebulizers with impactors.

FIG. 11 is a graph of droplet size distributions (differential concentration vs. droplet diameter measured in um) produced by various combinations of nebulizers with or without impactors A-D. Differential concentration is measured in d (#/cm$^3$) per d log (D$_p$). The graph includes lines illustrating fits of the PSD to a log-normal distribution. The droplet size distributions were measured by forming an aerosol from a sucrose solution, drying the droplets, measuring the residue PSD and calculating the droplet PSD using the equations above. The graph shows that Combination D has the best distribution in that it has the smallest and most uniform droplets, and virtually no droplets are larger than 10 um.

Figure 12:
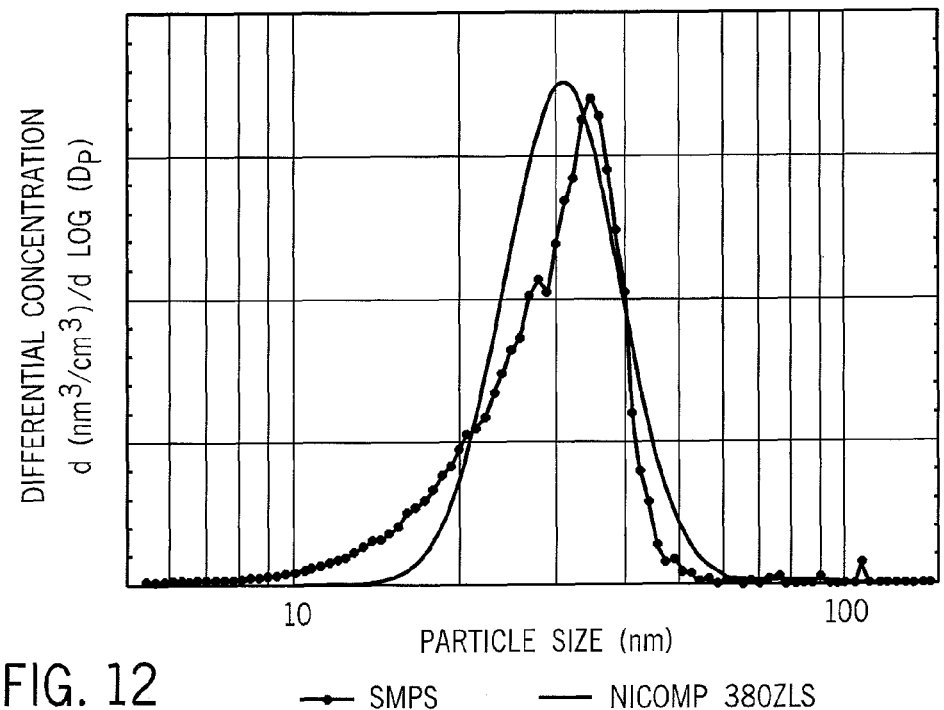
FIG. 12 is a graph of differential concentration versus particle size, which shows the ability to size 30 nm particle PSL.

FIG. 12 is a graph of differential residual concentration (d(nm$^3$/cm$^3$)/d log(D$_p$)) versus particle size (in nm) which shows the ability to size 30 nm polystyrene latex (PSL) particles. One sizing was conducted with a Combination D apparatus (FIG. 11) with an SMPS detector. Another was conducted with a dynamic light scattering (DLS) instrument, more particularly with a NICOMP 380ZLS made by Particle Sizing Systems, Santa Barbara, Calif. The comparison shows generally good agreement. The Combination D apparatus with SMPS analyzer permits measurement of actual number concentration. In contrast, DLS only provides relative concentrations.

Figure 13:
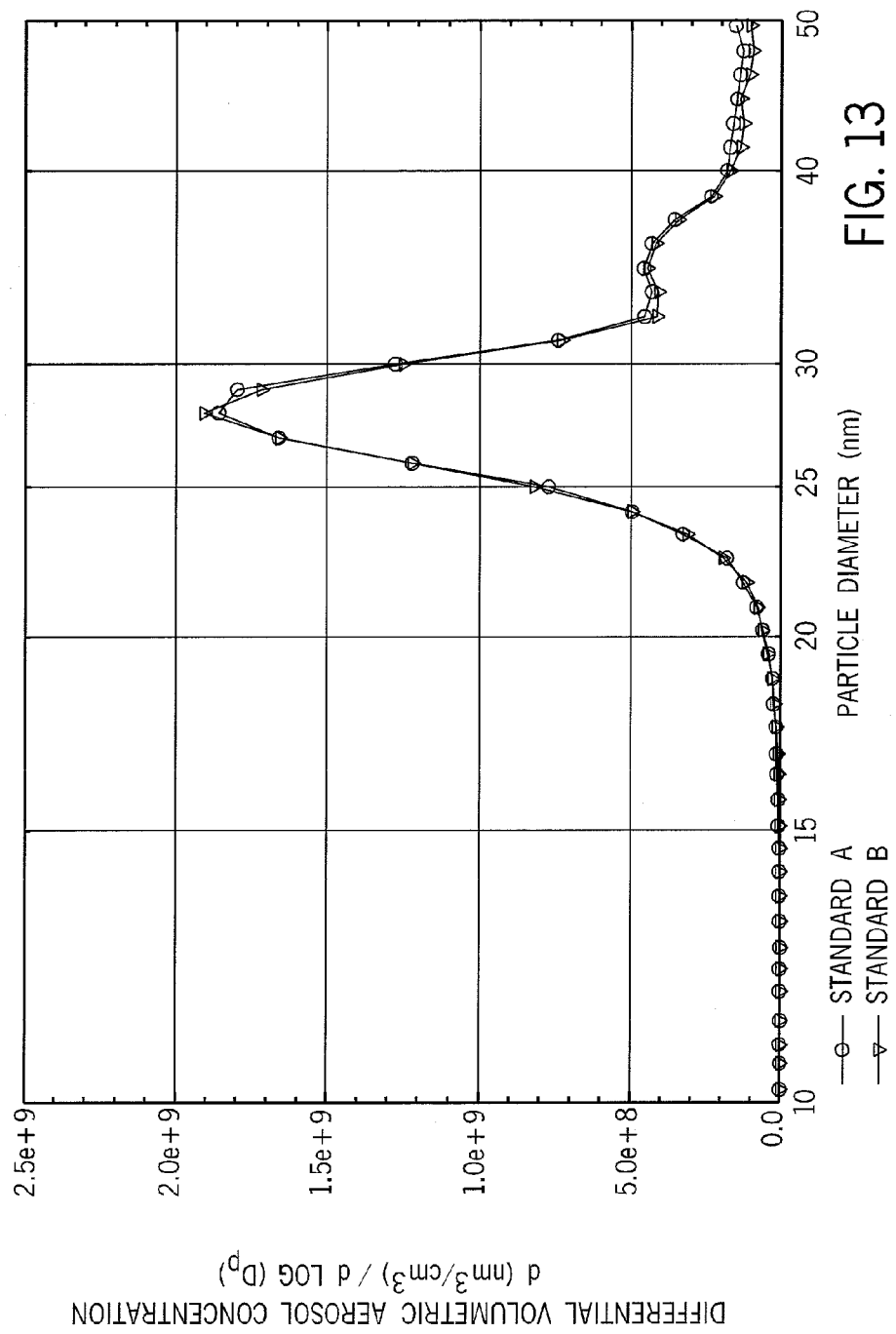
FIG. 13 is a graph of aerosol volumetric concentrations measured using standards containing $5.0 \times 10^{17}$ nm3/mL of silica particles.

Number concentrations can be measured directly by assemblies like Combination D with SMPS analyzer by calibrating the instrument liquid sampling flow rate using a colloidal suspension with a known volume concentration of pNVR and very little dNVR. Calibration is performed by inputting the suspension into Combination D with SMPS analyzer under controlled conditions and measuring the resulting volume-weighted PSD and calculating the liquid sampling rate using equation 5:

$$F_l = (C_{pa}/C_{pl})F_a \quad (5)$$

Where $F_l$ is the instrument liquid sampling flow rate, $C_{pa}$ is the volume concentration of particles in the aerosol, $C_{pl}$ is the volume concentration of particles in the suspension, and $F_a$ is the aerosol flow rate. FIG. 13 shows the mass distribution measured following input of $5.0 \times 10^{17}$ nm$^3$/mL suspensions of silica particles into, combination D with SMPS analyzer. In this case the liquid sampling flow rate was found to be 0.205 µL/min.

Figure 14B:
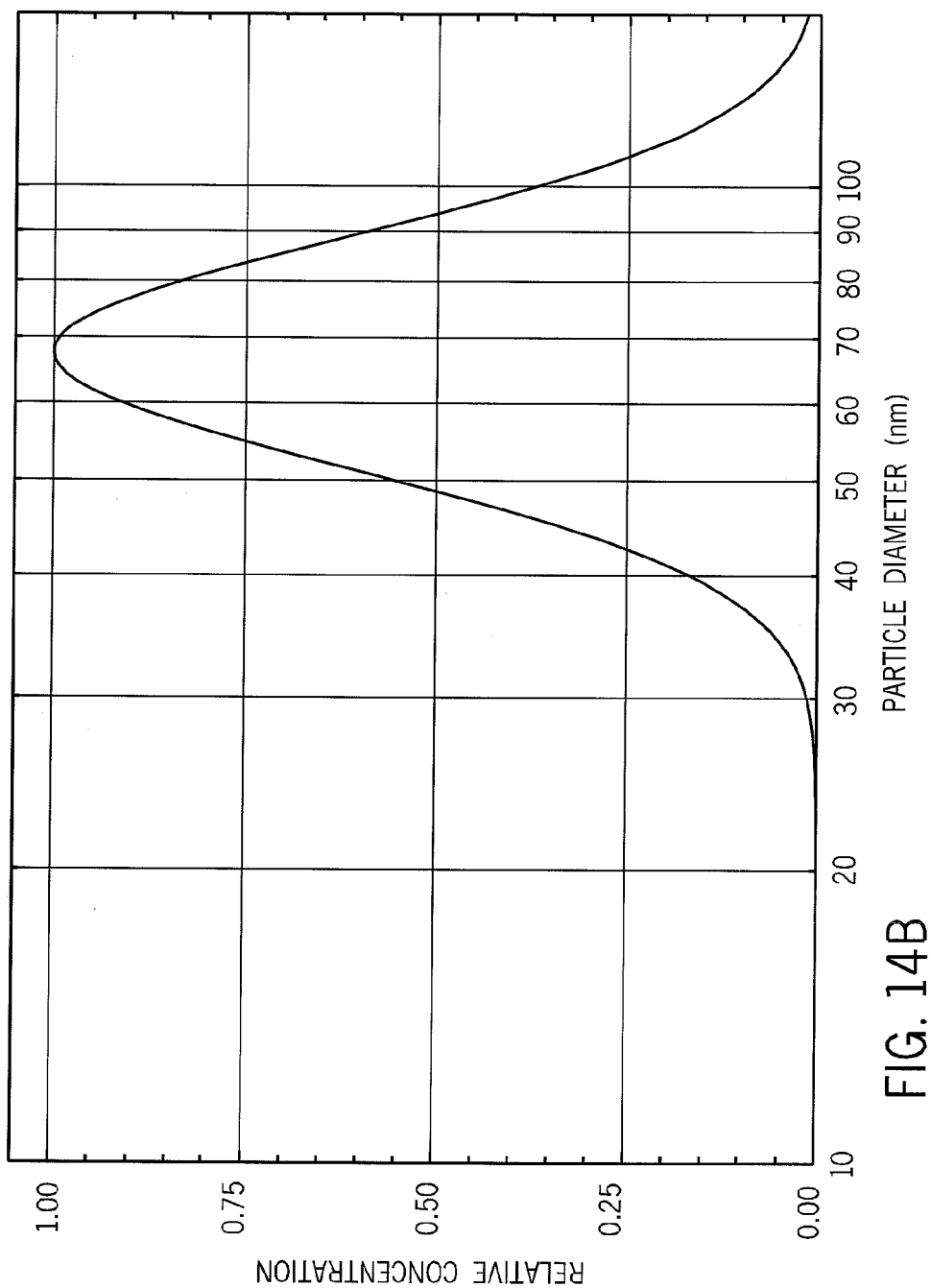
FIG. 14B shows pNVR particle size distributions in Colloidal Dispersion A measured using dynamic light scattering.
Figure 14C:
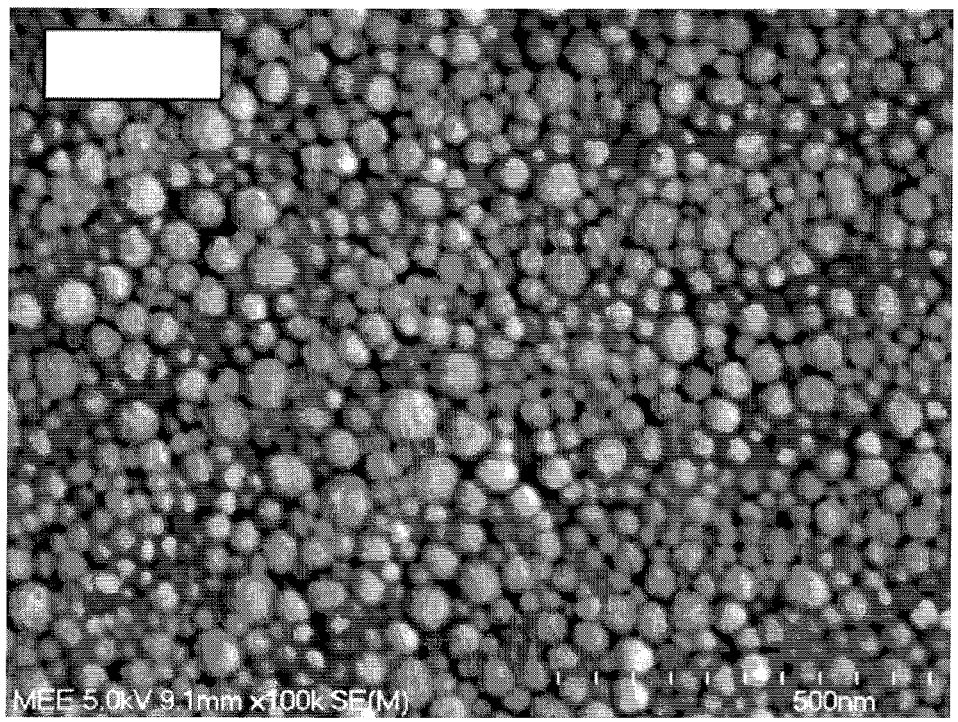
FIG. 14C shows particles in Colloidal Dispersion A imaged using Scanning Electron Microscopy.

The Combination D apparatus with SMPS analyzer also provides a more detailed measurement of PSD than DLS that most often assumes that the particles in the colloidal suspension are log-normally distributed. FIG. 14A is a graph of differential volume concentration vs. particle diameter for a colloidal dispersion measured using a Combination D apparatus with an SMPS detector. FIG. 14B shows the PSD measured using DLS and FIG. 14C shows images of the particles in the slurry from scanning electron microscopy (SEM). The Combination D apparatus with SMPS analyzer and the SEM analyses both indicate that the particles have a trimodal distribution; an aspect of the distribution that was not detected by the DLS analysis.

Figure 15A:
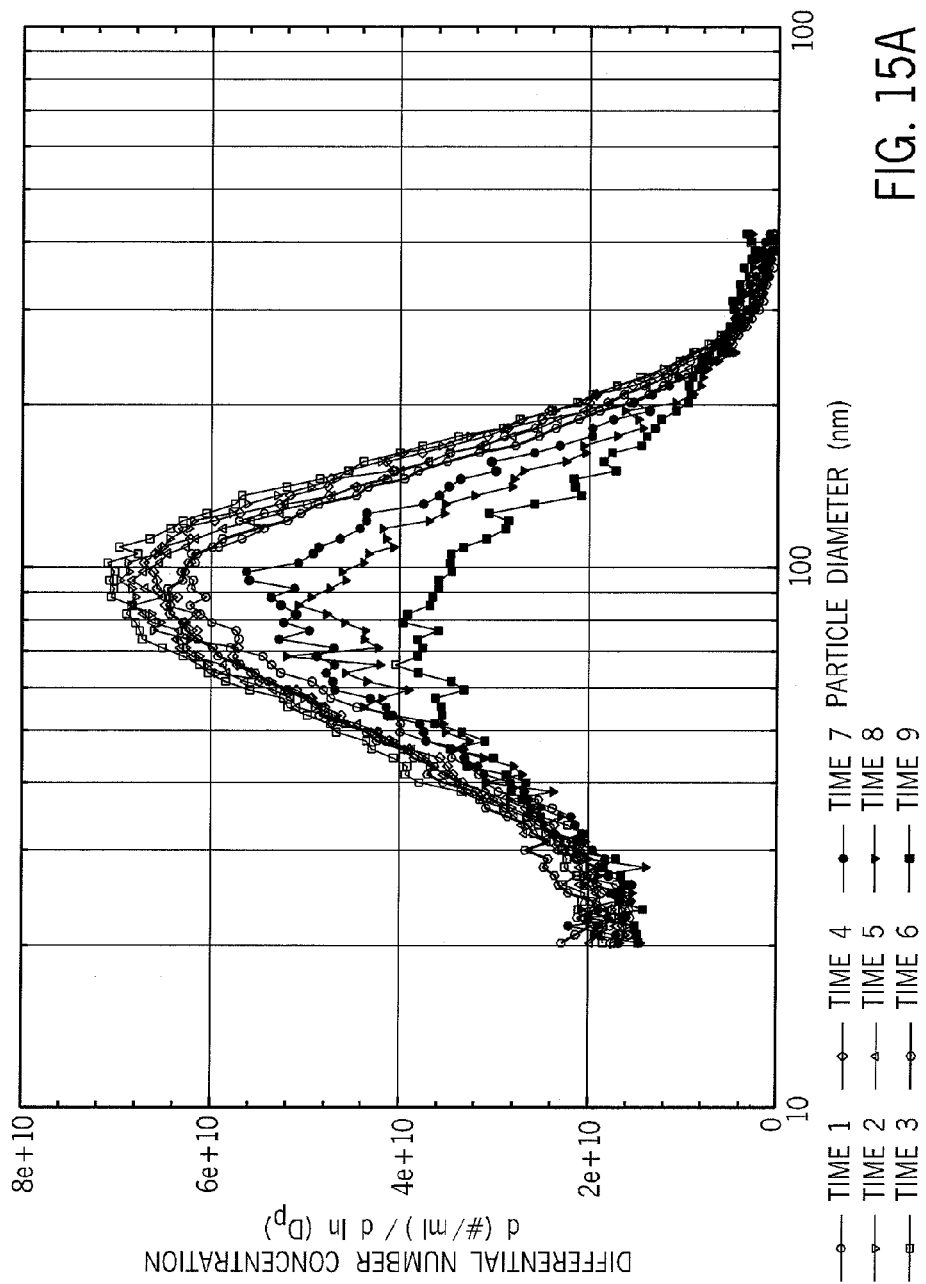
FIG. 15A shows the change in slurry number-weighted PSD over time during handling as measured using Combination D apparatus with an SMPS analyzer via a graph of differential number concentration versus particle diameter.
Figure 15C:
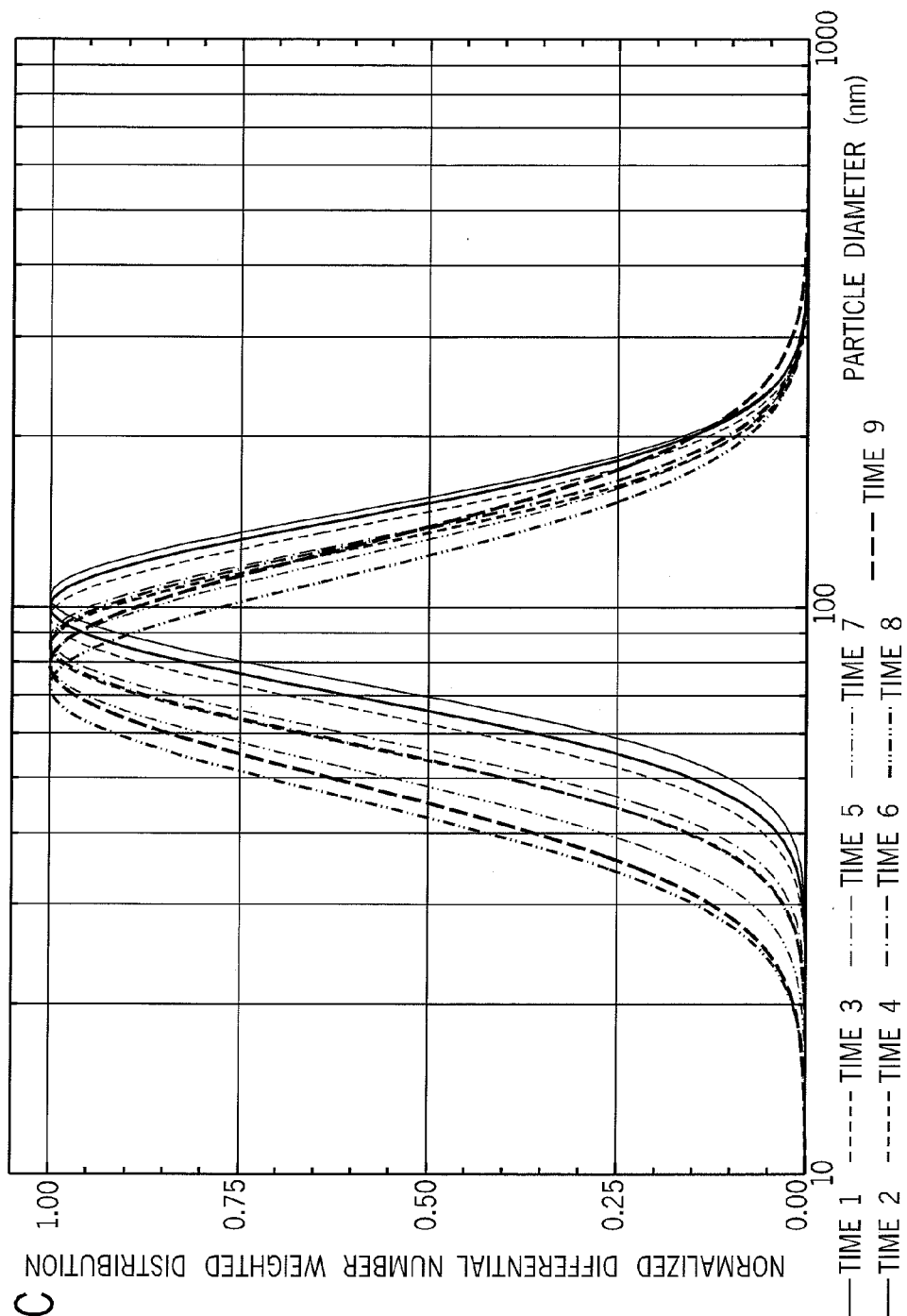
FIG. 15C shows the change in slurry PSD over time during handling as measured using Dynamic Light Scattering via a graph of differential number concentration versus particle diameter.

Measurement of actual number concentration measurement also allows determination of changes in PSD that are undetectable using instruments that only measure relative concentrations. FIGS. 15A and 15B show changes in slurry number-weighted and volume-weighted PSD over time during handling via graphs of differential concentration versus particle diameter. Successive times 1-9 are graphed. The number and volume of smaller particles decrease over time while the number and mass of larger particles (i.e. greater than approximately 250 nm) increases. This indicates that particle agglomeration is occurring due to handling. These changes were not detected by DLS (FIG. 15C).

Figure 16A:
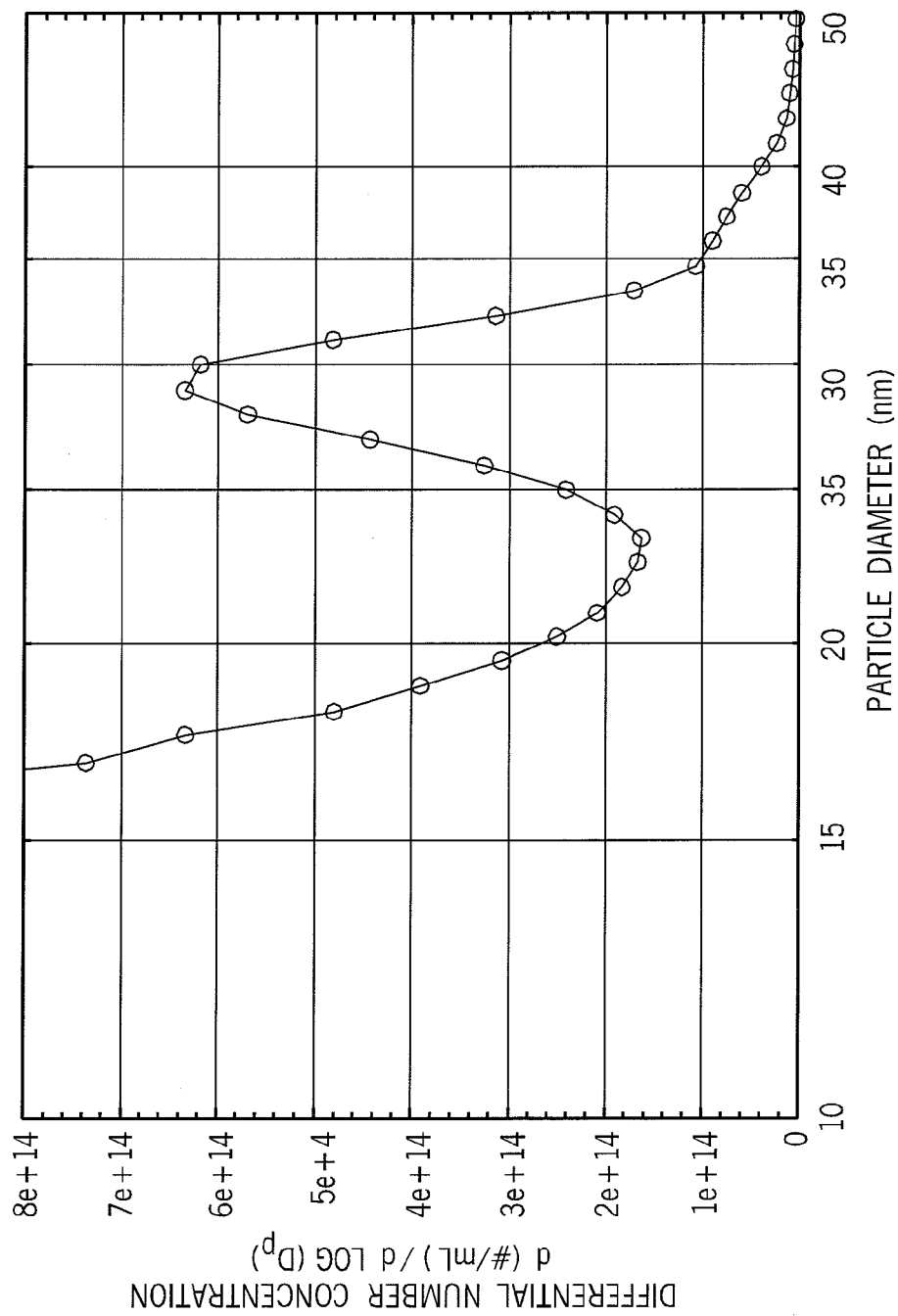
FIG. 16A shows particle concentration measurement of a liquid containing 0.1% by weigh pNVR silica particles and 1% by weight dNVR following a 2000:1 dilution.
Figure 17:
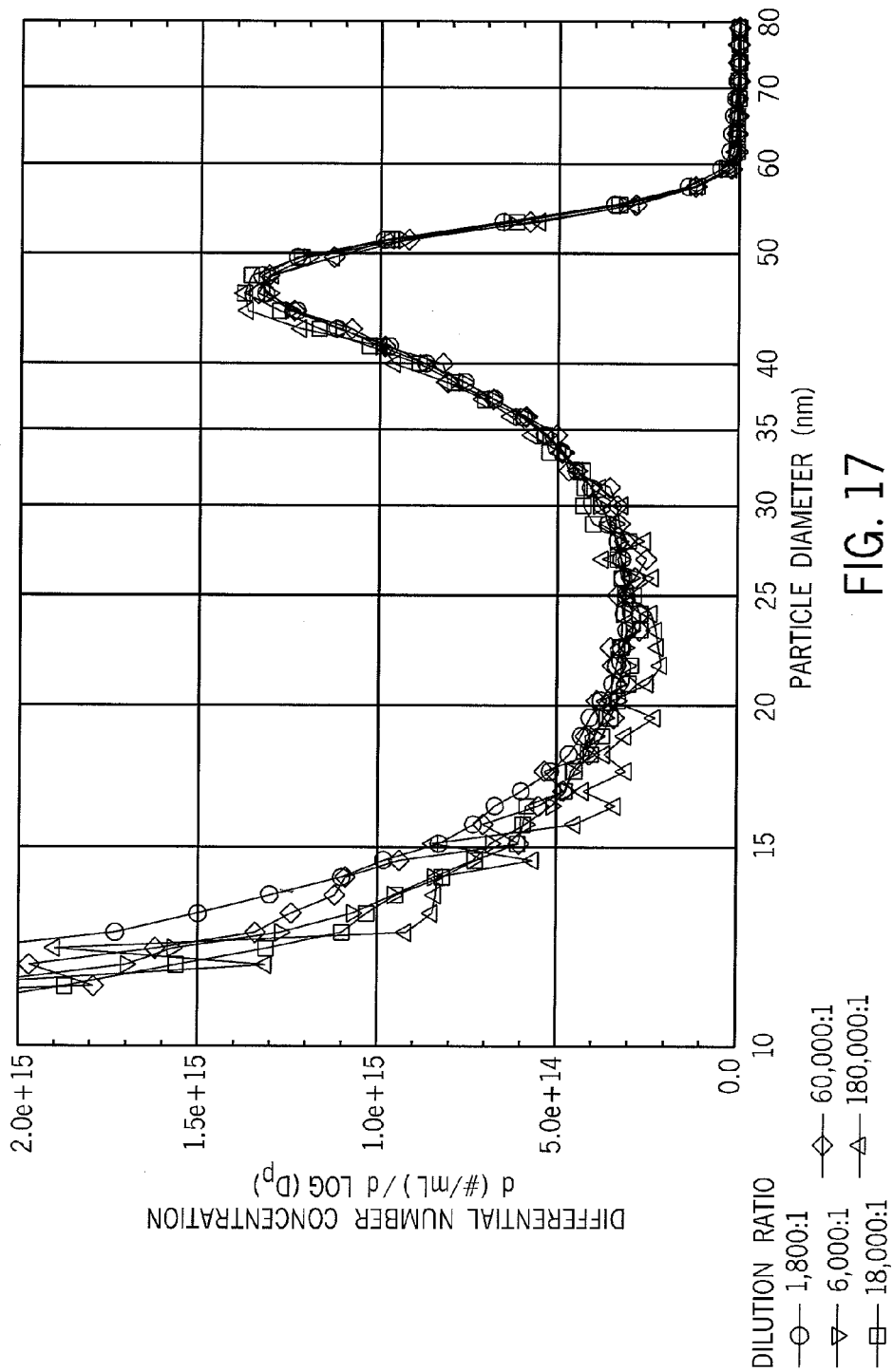
FIG. 17 shows particle concentration measurements of a liquid containing 2 populations of pNVR particles following different dilution ratios

FIG. 16A is a graph of the PSD from a colloidal dispersion of silica particles containing a high concentration of dNVR measured using Combination D with SMPS analyzer. In this case the dispersion contained 0.1% by weight pNVR and 1% by weight dNVR. The peak occurring ~29 nm is due to the pNVR while the high concentration of smaller particles results from the dNVR. There is poor separation between the pNVR and dNVR signals. However, by diluting the dispersion prior to input into the Combination D/SMPS analyzer separation can easily be achieved as shown in FIG. 16B. The separation does not occur if the smaller particle signal is due to a bimodal distribution of pNVR particles as shown in FIG. 17.

Figure 18B:
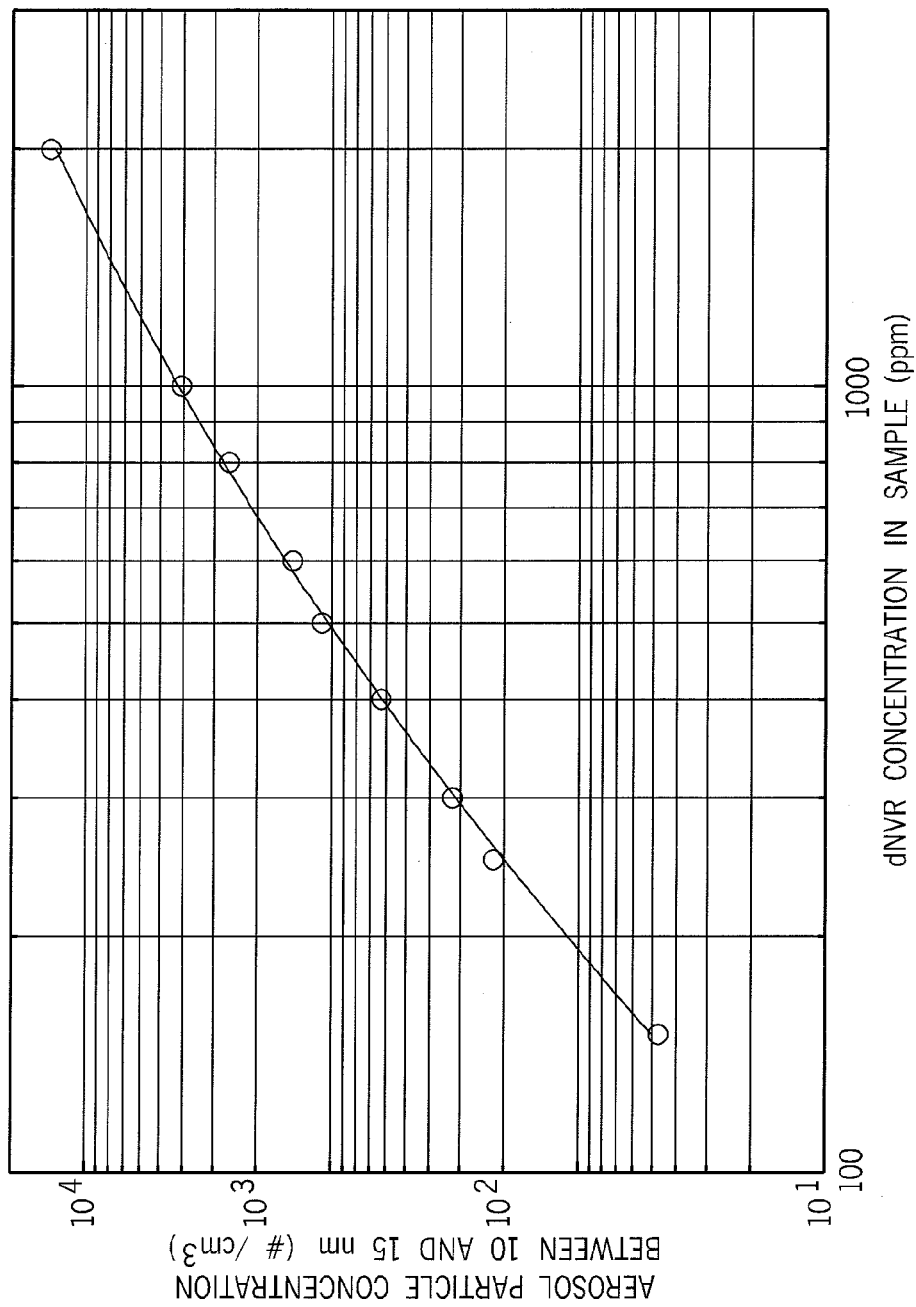
FIG. 18B shows the relationship between aerosol particle concentrations and dNVR concentrations in a liquid containing pNVR silica particles.

FIG. 18A is a graph showing measurements of a colloidal suspension of silica particles containing different concentrations of dNVR. The concentration of small particles is seen to increase with increasing dNVR concentration. The increase is monotonic with concentration as shown in FIG. 18B.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A method for analyzing dissolved and particulate residues in a liquid, the liquid being in a colloidal suspension, comprising the steps of:
    a. forming an aerosol containing droplets from the liquid,
    b. isolating small, uniformly sized droplets from the droplets, the small, uniformly sized droplets being less than 10 um in diameter,
    c. removing liquid from the small, uniformly sized droplets to form dissolved residue particles and particulate residue particles,
    d. analyzing dissolved and particulate residue particles by counting and sizing, and
    e. determining a liquid volumetric inspection rate of the method by inputting a colloidal suspension with known volumetric concentration of particulate residue and measuring the volumetric concentration of particulate residue in the aerosol produced by the method;
    f. wherein the method measures dissolved residue concentration and particulate residue particle concentration and size distribution in the colloidal suspension, the liquid and particles being in the colloidal suspension.

2. The method of claim 1, wherein the median diameter of small, uniformly sized droplets is less than 1 um, and the geometric standard deviation of the small, uniformly sized droplets is smaller than or equal to 1.5.

3. The method of claim 1, wherein the step of forming an aerosol comprises the steps of:
    i. inputting the liquid to a mixing zone,
    ii. inputting pressurized gas to the mixing zone; and
    iii. restricting output from the mixing zone to generate a backpressure in opposition to input of the liquid and the pressurized gas,
whereby the kinetic energy of mixing increases and decreases the size of droplets leaving the mixing zone.

4. The method of claim 1, wherein the step of isolating small, uniformly sized droplets less than 10 um. in diameter from the aerosol involves forming a thin, essentially hemispherical flow path of the aerosol droplets whereby droplets equal to or larger than 10 um in diameter leave the flow path and are impacted and removed.

5. The method of claim 1 wherein the step of removing liquid is accomplished by a process selected from the group of processes consisting of heating the aerosol, applying a stream of dilution air, applying a stream of heated air, heating the liquid, and fast evaporation.

6. The method of claim 1, wherein the step of analyzing residue particles is accomplished by a process selected from the group of processes consisting of optical particle counting and scanning mobility particle sizing.

7. A method of analyzing dissolved non-volatile residue and particulate non-volatile residue in a colloidal suspension, comprising the steps of:
    a. forming an aerosol containing droplets from the colloidal suspension and isolating small, uniformly sized droplets less than 10 um. in diameter from the droplets by:
        i. inputting the suspension to a mixing zone,
        ii. inputting pressurized gas to the mixing zone,
        iii. restricting output from the mixing zone to generate a backpressure in opposition to input of the suspension and the pressurized gas, whereby the kinetic energy of mixing increases and decreases the size of small droplets leaving the mixing zone, and
        iv. forming a thin essentially hemispherical flow path of droplets leaving the mixing zone whereby droplets equal to or larger than 10 um in diameter leave the flow path and are impacted and removed;
    b. removing liquid from the small, uniformly sized droplets less than 10 um. in diameter by evaporating them to a predetermined dryness to form dissolved residue particles separate and distinct from particulate residue particles;
    c. analyzing residual particles by counting and sizing to measure the relative concentrations of the dissolved and particulate residues and to measure the particle size distribution of the particulate residue particles; and
    d. determining the liquid volumetric inspection rate by inputting a colloidal suspension with a known volumetric concentration of particulate residue and measuring the volumetric concentration of particulate residue in the aerosol produced by steps a-c of the method.

8. A method for analyzing dissolved and particulate residues in a liquid, comprising the steps of:
    a. forming an aerosol containing droplets from the liquid, by the steps of:
        i. inputting the liquid to a mixing zone,
        ii. inputting pressurized gas to the mixing zone; and
        iii. restricting output from the mixing zone togenerate a backpressure in opposition to input of the liquid and the pressurized gas,
    whereby the kinetic energy of mixing increases and decreases the size of droplets leaving the mixing zone,
    b. isolating uniformly sized droplets from the droplets,
    c. removing liquid from the uniformly sized droplets to form dissolved residue particles and particulate residue particles, and
    d. analyzing dissolved and particulate residue particles by counting and sizing.

9. A method for analyzing dissolved and particulate residues in a liquid, comprising the steps of:
    a. forming an aerosol containing droplets from the liquid,
    b. isolating small, uniformly sized droplets less than 10 um in diameter from the droplets, by forming a thin, essentially hemispherical flow path of the aerosol droplets whereby large droplets equal to or greater than 10 um in diameter leave the flow path and are impacted and removed, c. removing liquid from the uniformly sized droplets to form dissolved residue particles and particulate residue particles, and d. analyzing dissolved and particulate residue particles by counting and sizing.

* * * * *